(12) United States Patent
Raz et al.

(10) Patent No.: US 6,893,821 B2
(45) Date of Patent: May 17, 2005

(54) AGENTS THAT MODULATE DNA-PK ACTIVITY AND METHODS OF USE THEREOF

(75) Inventors: Eyal Raz, Del Mar, CA (US); Augusto Lois, Escondido, CA (US); Kenji Takabayashi, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 378 days.

(21) Appl. No.: 09/848,986

(22) Filed: May 4, 2001

(65) Prior Publication Data

US 2003/0176373 A1 Sep. 18, 2003

Related U.S. Application Data

(60) Provisional application No. 60/262,321, filed on Jan. 17, 2001, and provisional application No. 60/202,274, filed on May 5, 2000.

(51) Int. Cl.⁷ .......................... C12Q 1/68; C12N 15/00; C12N 15/63; C12N 1/20; C07H 21/04; C07H 21/00; A61K 38/00; C07K 1/00
(52) U.S. Cl. ..................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1; 536/23.1; 536/24.1; 536/24.5; 530/300; 530/350
(58) Field of Search .................. 435/6, 70.1, 320.1, 435/91.1, 91.2; 536/23.4, 22.1

(56) References Cited

U.S. PATENT DOCUMENTS 6,441,158 B1 * 8/2002 Dynan ....................... 536/24.5

FOREIGN PATENT DOCUMENTS

| WO | WO 99/11275 | 3/1999 |
| WO | WO 99/33971 | 7/1999 |
| WO | WO 00/67023 | 11/2000 |

OTHER PUBLICATIONS

Muller, et al. Blood 92(7):2213–2219, 1998.*
Lees–Miller et al., Molecular and Cellular Biology 10(12):6472–6481, 1990.*
Finnie, et al, Proc. Natl. Acad. Sci. USA 92:320–324, 1995.*
Han, et al., Journal of Biological Chemistry 271:14098–14104, 1996.*
Klinman, et al., Proc Natl Acad Sci USA 93:2879–2883, 1996.*
Munoz, et al., Molecular and Cellular Biology 18:5797–5808 1998.*
Krieg, et al., Nature 374:546–549, 1995.*
Anderson (1993) "DNA damage and the DNA–activated protein kinase." *TIBS*, vol. 18: 433–437.
Anderson et al. (1998) "The Nuclear Serine/Threonine Protein Kinase DNA–PK." *Critical Reviews in Eukaryotic Gene Expression*, vol. 2(4): 283–314.
Basu et al. (1998) "The DNA Dependent Protein Kinase Participates in the Activation of NFKB Following DNA Damage." *Biochemical and Biophysical Research Communication*, vol. 247:79–83.

(Continued)

*Primary Examiner*—Jezia Riley
*Assistant Examiner*—Arun Chakrabarti
(74) *Attorney, Agent, or Firm*—Paula A. Borden; Carol L. Francis; Bozicevic, Field & Francis, LLP

(57) ABSTRACT

The present invention provides methods for modulating cell death in a eukaryotic cell, and methods for reducing DNA damage in a eukaryotic cell. The methods generally comprise modulating a biological activity of DNA-PK in a cell. The invention further provides methods of treating a condition related to cell death in an individual. The invention further provides methods of identifying agents which modulate a biological activity of DNA-PK, as well as agents identified by the methods. Methods of modulating an immune response using an identified agent are also provided.

6 Claims, 14 Drawing Sheets

OTHER PUBLICATIONS

Boulton et al. (1998) "Components of the Ku–dependent non–homologous end–joining pathway are involved in telomeric length maintenance and telomeric silencing." *The EMBO Journal*, vol. 17(6): 1819–1828.

Casellas et al. (1998) "Ku80 is required for immunoglobulin isotype switching." *The EMBO Journal*, vol. 17 (8):2404–2411.

Chu (1997) "Double Strand Break Repair." *The Journal of Biological Chemistry*, vol. 272(39):24097–24100.

Cohen et al. (1992) "Apoptosis and Programmed Cell Death in Immunity." *Annu. Rev. Immunol*., vol. 10:267–93.

Duvall et al. (1986) "Death and the cell." *Immunology*, vol. 7(4):115–119.

Dynan et al. (1998) "Interaction of Ku protein and DNA–dependent protein kinase catalytic subunit with nucleic acids." *Nucleic Acids Research*, vol. 26 (7):1551–1559.

Gerschenson et al. (1992) "Apoptosis: A different type of cell death." *FASEB J*., vol. 6:2450–2455.

Giffin et al. (1997) "Sequence–specific DNA Binding and Transcription Factor Phosphorylation by Ku Autoantigen/DNA–dependent Protein Kinase." *The Journal of Biological Chemistry*, vol. 272 (9):5647–5658.

Hammarsten et al. (2000) "Activation of DNA–dependent Protein Kinase by Single–stranded DNA Ends. " *The Journal of Biological Chemistry*, vol. 275 (3):1541–1550.

Klinman et al. (1999) "Immune Recognition of Foreign DNA: A Cure for Bioterrorism?" *Immunity*, vol. 11:123–129.

Leuther et al. (1999) "Structure of DNA–dependent protein kinase: implications for its regulation by DNA." *The EMBO Journal*, vol. 18 (5):1114–1123.

MacFarlene et al. (1997) "Unmethylated CpG–containing oligodeoxynucleotides inhibit apoptosis in WEHI231 B lymphocytes induced by several agents: evidence for blockade of apoptosis at a distal signalling step." *Immunology*, vol. 91:586–593.

Medzhitov et al. (1997) "Innate Immunity: The Virtues of a Nonclonal System of Recognition." *Cell*, vol. 91:295–298.

Mimori et al. (1986) "Mechanism of Interaction between Ku Protein and DNA." *The Journal of Biological Chemistry*, vol. 261 (22):10375–10379.

Mimori et al. (1981) "Characterization fo a High Molecular Weight Acidic Nuclear Protein Recognized by Autoantibodies in Sera from Patients with Polymyositis–Scleroderma Overlap." *J. Clin. Invest*., vol. 68:611–620.

Morano et al. (1999) "Heat Shock Factor Function and Regulation in Response to Cellular Stress, Growth, and Differentiation Signals." *Gene Expression*, vol. 7:271–282.

Nueda et al. (1999) "DNA–dependent Protein Kinase Protects against Heat–induced Apoptosis." *The Journal of Biological Chemistry*, vol. 274 (21):14988–14996.

Reeves (1992) "Antibodies to the p70/p80 (ku) Antigens in systemic Lupus Erythematosus." *Rhem. Dis. Clin. North Am.*, vol. 18 (2):391–414.

Roman et al. (1997) "Immunostimulatory DNA sequences function as T helper–1–promoting adjuvants." *Nature Medicine*, vol. 3 (8):849–854.

Ruiz et al. (1999) "OBA/Ku86: DNA Binding Specificity and Involvement in Mammalian DNA Replication." *Molecular Biology of the Cell*, vol. 10:567–580.

Shao et al. (1999) "Replication–mediated DNA damage by camptothecin induces phosphorylation of RPA bny DNA–dependent protein kinase and dissociates RPA: DNA–PK complexes." *The EMBO Journal*, vol. 18 (5):1397–1406.

Tsuchiya et al. (1998) "Ku Antigen Binds to Alu Family DNA." *J. Biochem*., vol. 123:120–127.

Weaver (1996) "Regulation and Repair of Double–Strand DNA Breaks." *Critical Reviews in Eukaryotic Gene expression*, vol. 6 (4):345–375.

Yi et al. (1999) "CpG DNA rescues B cells from apoptosis by activating NFKB and preventing mitochondrial membrane potential disruption via a chloroquine–sensitive pathway." *International Immunology*, vol. 11 (12):2015–2024.

Yi et al. (1998) "CpG Oliogodeoxyribonucleotides Rescue Mature Spleen B Cells from Spontaneous Apoptosis and Promote cell Cycle Entry." *The Journal of Immunology*, vol. 160: 5898–5906.

Yi et al. (1996) "CpG DNA Rescue of Murine B Lymphoma Cells from Anti–IgM–Induced Growth Arrest and Programmed Cell Death is Associated with Increased Expression of c–myc and bcl–x," *The Journal of Immunology*, vol. 157:4918–4925.

Yi et al. (1998) "CpG DNA Rescue from Anti–IgM–Induced WEHI–231 B Lymphoma Apoptosis via Modulation of IκBα and Sustained Activation of Nuclear Factor–κB/c–Rel." *The Journal of Immunology*, vol. 160: 1240–1245.

Zou et al. (2000) "Assembly of a Complex Containing Cdc45p, Replication Protein A, and Mcm2p at Replication Origins Controlled by S–Phase Cyclin–Dependent Kinases and Cdc7p–Db4p Kinase." *Molecular and Cellular Biology*, vol. 20 (9):3086–3096.

Genbank Acession No. A32626, deposited Nov. 5, 1999.

Genbank Acession No. NP_001460, deposited Oct. 31,2000.

Genbank Acession No. P12956, deposited Oct. 1, 2000.

Genbank Acession No. P13010, deposited Oct. 1, 2000.

Genbank Acession No. S25149, deposited Aug. 26, 1999.

* cited by examiner

FIG. 1A
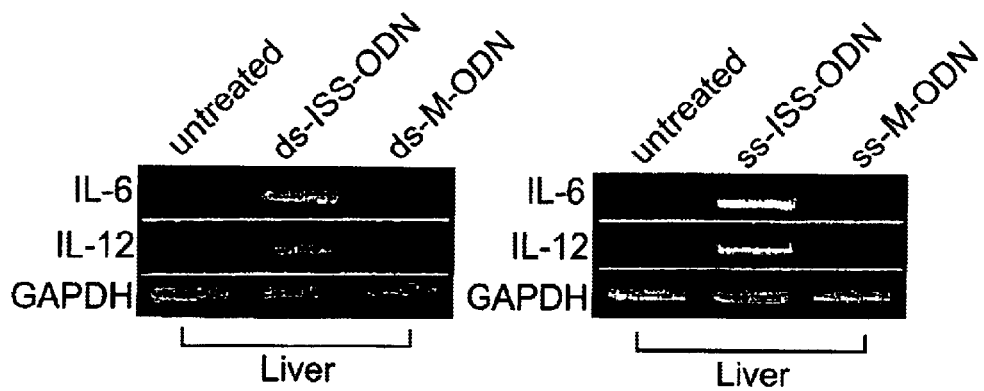
FIG. 1B
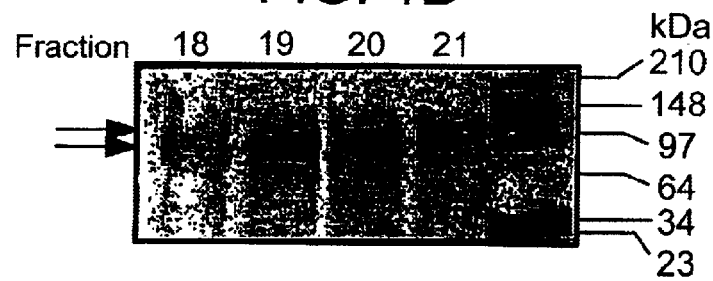
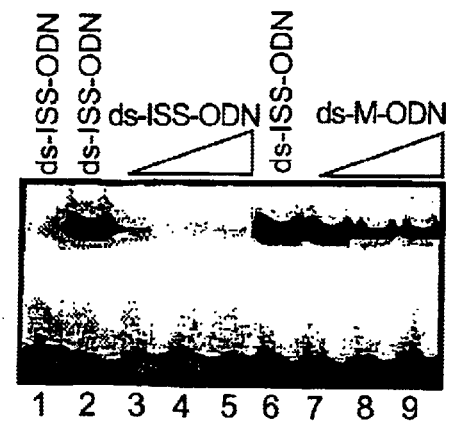
FIG. 1C
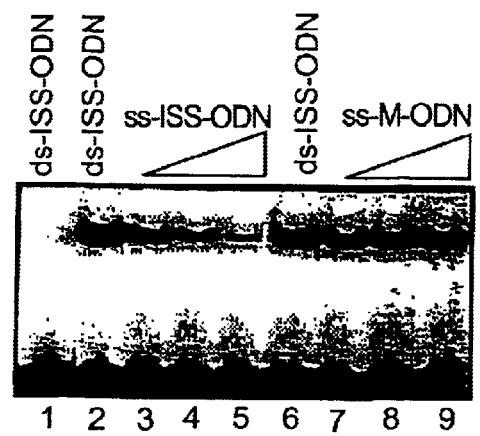
FIG. 1D

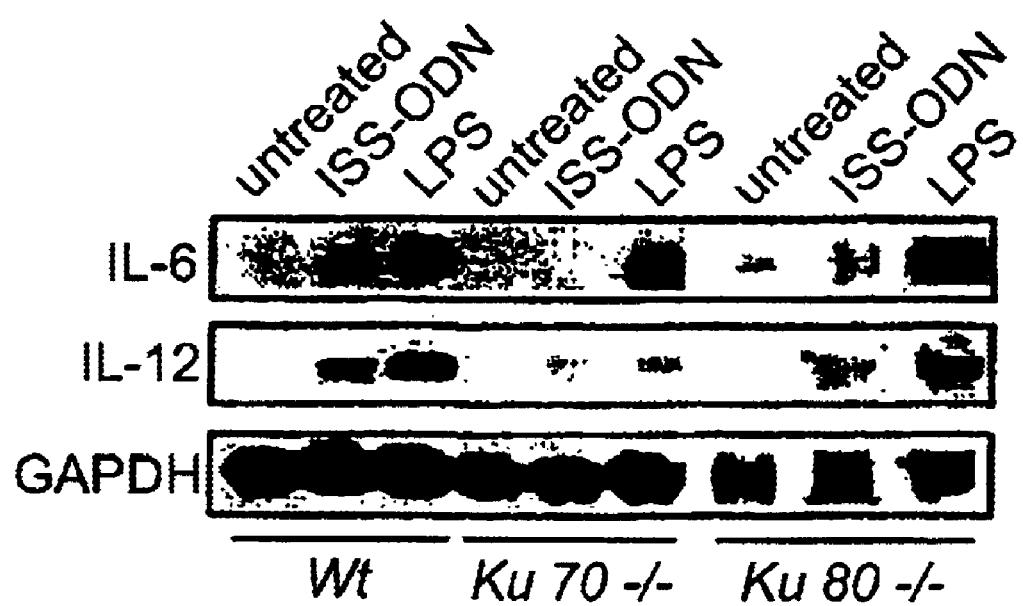

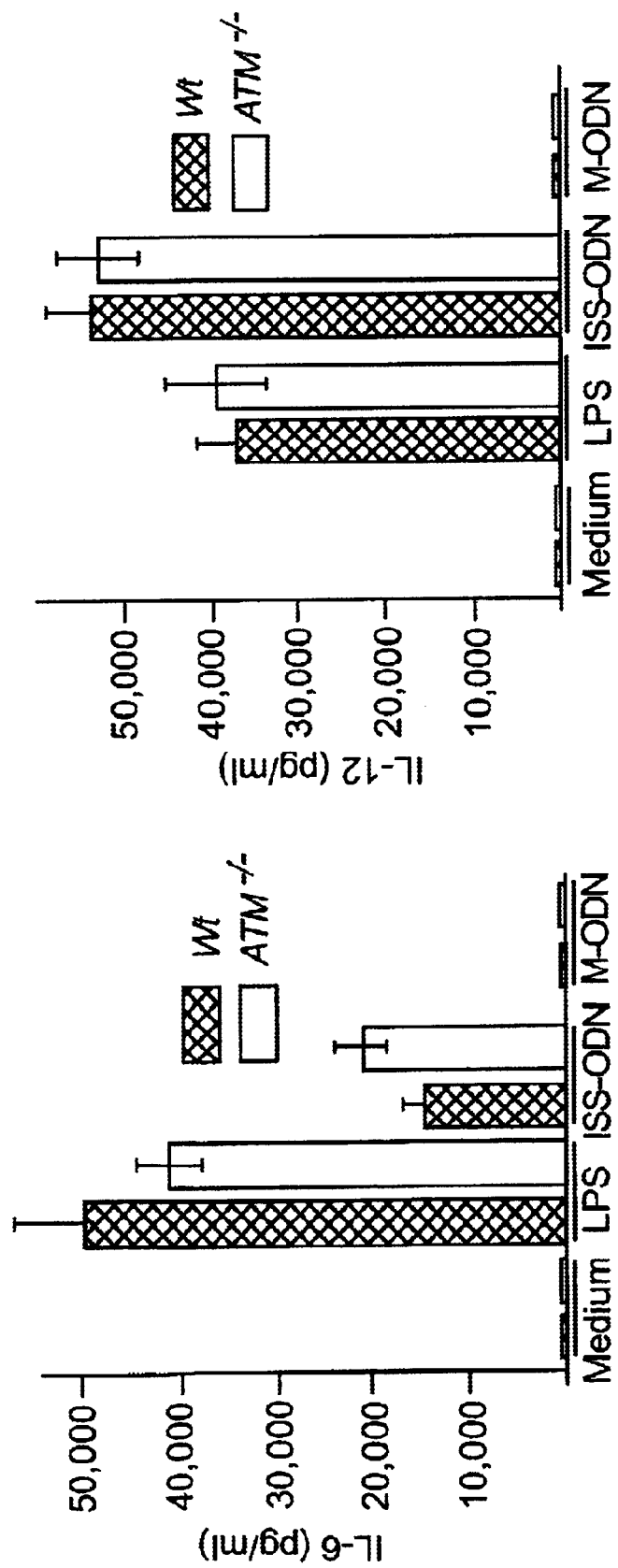

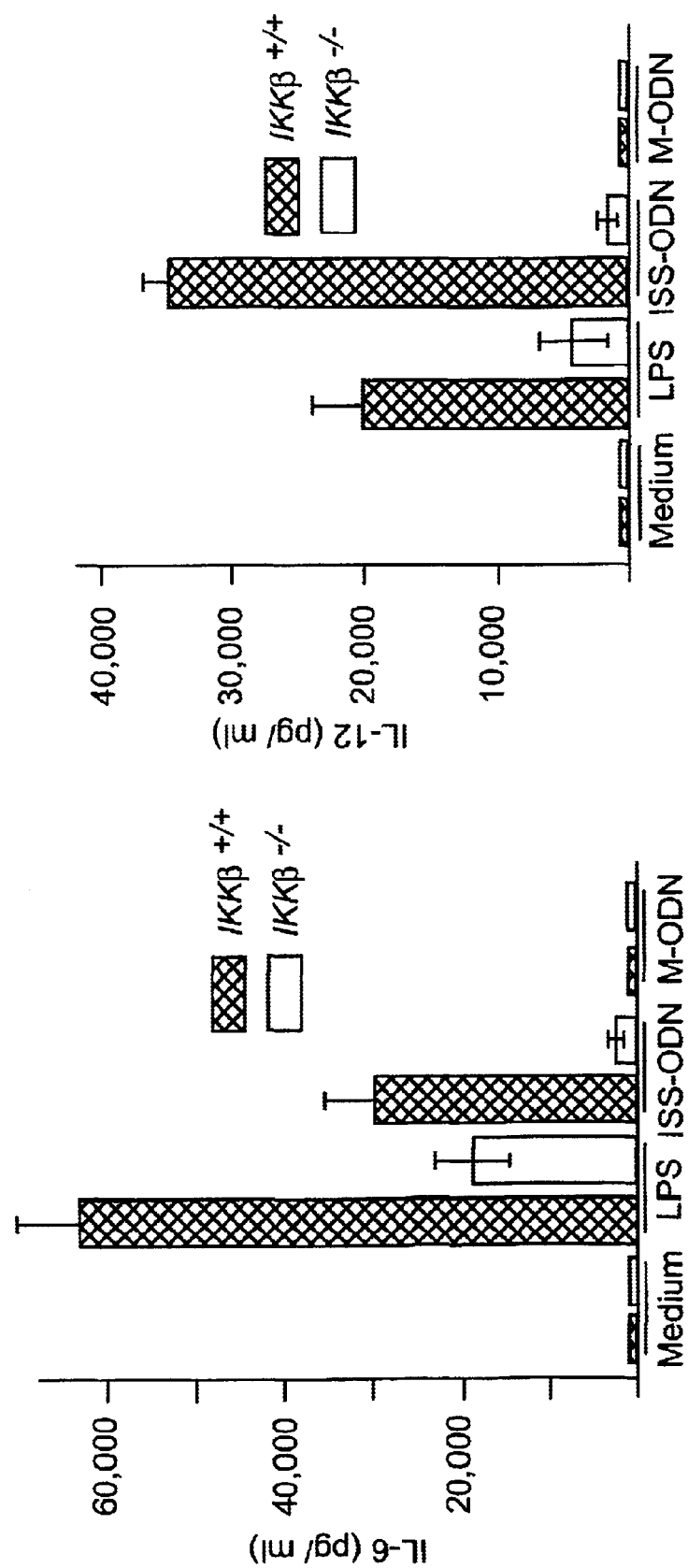

HSP70

HSC70

HSP96

G3PDH

HSP70

G3PDH

SEQUENCE LISTING

```
<160> NUMBER OF SEQ ID NOS: 21

<210> SEQ ID NO 1
<211> LENGTH: 22
<212> TYPE: DNA
<213> ORGANISM: Artificial Sequence
<220> FEATURE:
<223> OTHER INFORMATION: ISS-ODN

<400> SEQUENCE: 1
tgactgtgaa cgttcgagat ga                                              22

<210> SEQ ID NO 2
<211> LENGTH: 20
<212> TYPE: DNA
<213> ORGANISM: Artificial Sequence
<220> FEATURE:
<223> OTHER INFORMATION: M-ODN

<400> SEQUENCE: 2
tgactgtgaa ccttagagaa                                                 20

<210> SEQ ID NO 3
<211> LENGTH: 25
<212> TYPE: DNA
<213> ORGANISM: Artificial Sequence
<220> FEATURE:
<223> OTHER INFORMATION: IL-6 primer sense sequence

<400> SEQUENCE: 3
atgaagttcc tctctgcaag agact                                           25

<210> SEQ ID NO 4
<211> LENGTH: 24
<212> TYPE: DNA
<213> ORGANISM: Artificial Sequence
<220> FEATURE:
<223> OTHER INFORMATION: IL-6 primer antisense sequence

<400> SEQUENCE: 4
cactaggttt gccgagtaga tctc                                            24

<210> SEQ ID NO 5
<211> LENGTH: 21
<212> TYPE: DNA
<213> ORGANISM: Artificial Sequence
<220> FEATURE:
<223> OTHER INFORMATION: IL-12p40 primer sense sequence

<400> SEQUENCE: 5
gggacatcat caaaccagac c                                               21

<210> SEQ ID NO 6
<211> LENGTH: 21
<212> TYPE: DNA
<213> ORGANISM: Artificial Sequence
```

```
<220> FEATURE:
<223> OTHER INFORMATION: IL-12p40 primer antisense sequence

<400> SEQUENCE: 6
gccaaccaag cagaagacag c                                              21

<210> SEQ ID NO 7
<211> LENGTH: 20
<212> TYPE: DNA
<213> ORGANISM: Artificial Sequence
<220> FEATURE:
<223> OTHER INFORMATION: GAPDH primer sense sequence

<400> SEQUENCE: 7
accacagtcc atgccatcac                                                20

<210> SEQ ID NO 8
<211> LENGTH: 20
<212> TYPE: DNA
<213> ORGANISM: Artificial Sequence
<220> FEATURE:
<223> OTHER INFORMATION: GAPDH primer antisense sequence

<400> SEQUENCE: 8
tccaccaccc tgttgctgta                                                20

<210> SEQ ID NO 9
<211> LENGTH: 22
<212> TYPE: DNA
<213> ORGANISM: Artificial Sequence
<220> FEATURE:
<223> OTHER INFORMATION: M-ODN

<400> SEQUENCE: 9
tgactgtgaa ccttagagat ga                                             22

<210> SEQ ID NO 10
<211> LENGTH: 22
<212> TYPE: DNA
<213> ORGANISM: Artificial Sequence
<220> FEATURE:
<223> OTHER INFORMATION: ISS-ODN

<400> SEQUENCE: 10
tgactgtgaa cgttagagat ga                                             22

<210> SEQ ID NO 11
<211> LENGTH: 22
<212> TYPE: DNA
<213> ORGANISM: Artificial Sequence
<220> FEATURE:
<223> OTHER INFORMATION: methylated ISS-ODN
<221> NAME/KEY: modified_base
<222> LOCATION: (11)...(11)
<223> OTHER INFORMATION: m5c

<400> SEQUENCE: 11
tgactgtgaa cgttagagat ga                                             22

<210> SEQ ID NO 12
<211> LENGTH: 22
<212> TYPE: DNA
<213> ORGANISM: Artificial Sequence
<220> FEATURE:
<223> OTHER INFORMATION: M-ODN

<400> SEQUENCE: 12
```

<210> SEQ ID NO 13
<211> LENGTH: 22
<212> TYPE: DNA
<213> ORGANISM: Artificial Sequence
<220> FEATURE:
<223> OTHER INFORMATION: control ODN

<400> SEQUENCE: 13
tgactgtgtt ccttagagat ga                                              22

<210> SEQ ID NO 14
<211> LENGTH: 22
<212> TYPE: DNA
<213> ORGANISM: Artificial Sequence
<220> FEATURE:
<223> OTHER INFORMATION: control ODN

<400> SEQUENCE: 14
tgactgtgaa tattagagat ga                                              22

<210> SEQ ID NO 15
<211> LENGTH: 20
<212> TYPE: DNA
<213> ORGANISM: Artificial Sequence
<220> FEATURE:
<223> OTHER INFORMATION: hsp70 primer sense sequence

<400> SEQUENCE: 15
gagatcatcg ccaacgacca                                                 20

<210> SEQ ID NO 16
<211> LENGTH: 20
<212> TYPE: DNA
<213> ORGANISM: Artificial Sequence
<220> FEATURE:
<223> OTHER INFORMATION: hsp70 primer antisense sequence

<400> SEQUENCE: 16
acagtctttc cgaggtatcg                                                 20

<210> SEQ ID NO 17
<211> LENGTH: 20
<212> TYPE: DNA
<213> ORGANISM: Artificial Sequence
<220> FEATURE:
<223> OTHER INFORMATION: hsc70 primer sense sequence

<400> SEQUENCE: 17
aatgaccagg gtaaccgcac                                                 20

<210> SEQ ID NO 18
<211> LENGTH: 20
<212> TYPE: DNA
<213> ORGANISM: Artificial Sequence
<220> FEATURE:
<223> OTHER INFORMATION: hsc70 primer antisense sequence

<400> SEQUENCE: 18
acagtctttc cgaggtatcg                                                 20

<210> SEQ ID NO 19
<211> LENGTH: 20
<212> TYPE: DNA
<213> ORGANISM: Artificial Sequence

```
<220> FEATURE:
<223> OTHER INFORMATION: hsp90 primer sense sequence

<400> SEQUENCE: 19
atgagggtcc tgtgggtgtt                                              20

<210> SEQ ID NO 20
<211> LENGTH: 20
<212> TYPE: DNA
<213> ORGANISM: Artificial Sequence
<220> FEATURE:
<223> OTHER INFORMATION: hsp90 primer antisense sequence

<400> SEQUENCE: 20
cacttcagct tggaaggcga                                              20

<210> SEQ ID NO 21
<211> LENGTH: 20
<212> TYPE: DNA
<213> ORGANISM: Artificial Sequence
<220> FEATURE:
<223> OTHER INFORMATION: ISS-ODN

<400> SEQUENCE: 21
tgactgaacg ttcgagatga                                              20
```

AGENTS THAT MODULATE DNA-PK ACTIVITY AND METHODS OF USE THEREOF

CROSS-REFERENCE

This application claims the benefit of U.S. Provisional Application Ser. No. 60/202,274, filed May 5, 2000, and U.S. Provisional Application Ser. No. 60/262,321, filed Jan. 17, 2001, both of which are incorporated by reference herein in their entirety.

STATEMENT REGARDING FEDERALLY SPONSORED RESEARCH

The United States Government may have certain rights in this application pursuant to National Institutes of Health Grant Nos. AI 40682, CA 56909, CA 31397, and CA78497.

FIELD OF THE INVENTION

This invention is in the field of control of cellular signaling, and in particular the use of immunomodulatory polynucleotides to modulate cell death.

BACKGROUND OF THE INVENTION

The innate immune response to an invading pathogen involves the effective and rapid recognition of highly conserved and repeated foreign structures such as those found in polysaccharides, lectins, complexed lipids (e.g., LPS) and double stranded (ds) RNA. Medzhitov and Janeway (1997) *Cell* 91:295. Recently, bacterial genomic DNA, plasmids and immunostimulatory oligodeoxynucleotides containing CpG dinucleotides in a particular base context (ISS-ODN or CpG motifs) have been shown to activate innate immunity. Klinman et al. (1999) *Immunity* 11:123. In contrast, mammalian DNA or methylated bacterial DNAs are inactive. ISS stimulate macrophages/monocytes to secrete IL-6 and IL-12, activate NK cells, induce B-cell proliferation and polyclonal IgM production and rescue B cells from apoptosis. Klinman et al. (1999) *Immunity* 11:123. Furthermore, when ISS is co-delivered with an antigen, it elicits cell-mediated immunity, which mimics the host immune response against viral infection. Roman et al. (1997) *Nature Med.* 8:849.

Ku protein was originally discovered as an autoantigen recognized by autoantibodies from the sera of certain patients with systemic autoimmune diseases. Mimori et al. (1981) *J. Clin. Invest.* 68:611–620; and Mimori and Hardin (1986) *J. Biol. Chem.* 261:10375–10379; and reviewed in Reeves et al. (1992) *Rhem. Dis. Clin. North Am.* 18:391–414. Ku antigen is a heterodimeric protein consisting of two polypeptides of approximately 70 kDa and 80 kDa. Ku antigen was subsequently shown to the regulatory component of DNA-dependent protein kinase (DNA-PK). Dynan and Yoo (1998) *Nucl. Acids Res.* 26:1551–1559.

Ku, which binds to double-stranded DNA breaks (DSB), is believed to play a role in targeting the DNA-PK complex to DSB for repair. Specifically, when bound to DNA, Ku interacts with and activates the DNA-PK catalytic subunit (DNA-PKcs). DNA-PKcs is believed to interact with and phosphorylate several DNA-binding proteins in vitro, such as replication protein A and the tumor suppressor protein p53, respectively, as well as other transcription factors. Anderson and Lees-Miller (1992) *Crit. Reviews in Euk. Gene Expression* 2:283; and Anderson (1993) *Trends Biochem. Sci.* 18:433. DNA-PK is thought to play a role in controlling gene regulation and cell growth. Ku has been reported to bind to various DNA sequences, including NRE1 (negative regulatory element 1) sequences from a viral LTR comprising repeats of 5'-GAAAG-3' (Giffin et al. (1997) *J. Biol. Chem.* 272:5647–5658); an Alu core element comprising the sequence 5'-GGAGGGC-3' (Tsuchiya et al. (1998) *J. Biochem.* 123:120–127; and a mammalian DNA origin of replication (Ruiz et al. (1999) *Mol. Biol. Cell* 10:567–580).

In addition to DSB repair, DNA-PK is also involved in V(D)J recombination, isotype switching, as well as telomere length maintenance and silencing. Weaver et al. (1996) *CRC Crit. Rev. Eukaryotic Gene Exp.* 6:345–375; Chu (1997) *J. Biol. Chem.* 272:24097–24100; Casellas et al. (1998) *EMBO J.* 17:2404–2411; and Boulton and Jackson (1998) *EMBO J.* 17:1819–1828. DNA-PK also participates in the activation of NFκB by ioninizing radiation. Basu et al. (1998) *Biochem. Biophys. Res. Comm.* 247:79–83.

Apoptosis, or programmed cell death (PCD) is a type of cell death that is fundamentally distinct from degenerative death or necrosis. It is an active process of gene-directed cellular self-destruction which in some instances, serves a biologically meaningful homeostatic function.

Apoptotic cell death is characterized primarily by internucleosomal DNA cleavage and chromatin condensation, and also by cellular shrinkage, cytoplasmic blebbing, and increased membrane permeability. Gerschenson et al. (1992) *FASEB J.* 6:2450–2455; and Cohen and Duke (1992) *Ann. Rev. Immunol.* 10:267–293. This can be contrasted to necrosis, which is cell death occurring as the result of severe injurious changes in the environment of infected cells. Necrosis is characterized by the swelling and rupturing of cells, the loss of membrane integrity, a random breakdown of DNA into fragments of variable size, and the phagocytosis of cellular debris by macrophages. The release of lysosomal enzymes damages neighboring cells, thus, cells die in groups. This produces an inflammatory response in tissue. Cell death by necrosis involves no direct RNA or protein synthesis. For a general review of apoptosis, see Tomei, L. D. and Cope, F. O. Apoptosis: The Molecular Basis of Cell Death (1991) Cold Spring Harbor Press, N.Y.; Tomei, L. D. and Cope, F. O. Apoptosis II: The Molecular Basis of Apoptosis in Disease (1994) Cold Spring Harbor Press, N.Y.; and Duvall and Wyllie (1986) *Immun. Today* 7:115–119.

Apoptosis can be activated by a number of intrinsic or extrinsic signals. These signals include the following: mild physical signals, such as ionization radiation, ultraviolet radiation, or hyperthermia; low to medium doses of toxic compounds, such as azides or hydrogen peroxides; chemotherapeutic drugs, such as etoposides and teniposides, cytokines such as tumour necrosis factors and transforming growth factors; infection with human immunodeficiency virus (HIV); and stimulation of T-cell receptors. Various pathological processes, such as hormone deprivation, growth factor deprivation, thermal stress and metabolic stress, induce apoptosis. (Wyllie, A. H., in Bowen and Lockshin (eds.) *Cell Death in Biology and Pathology* (Chapman and Hall, 1981), at 9–34).

Unregulated apoptosis can cause, or be associated with, disease. For example, unregulated apoptosis is involved in diseases such as cancer, heart disease, neurodegenerative disorders, autoimmune disorders, and viral and bacterial infections. Cancer, for example, not only triggers cells to proliferate but also blocks apoptosis. Cancer is partly a failure of apoptosis in the sense that the signal(s) for the cells to kill themselves by apoptosis are blocked.

In heart disease, damage caused by trauma (e.g, resulting in shock), and cardiac cells can be induced to undergo apoptosis. For example, cells deprived of oxygen after a heart attack release signals that induce apoptosis in cells in the heart. Apoptosis may also be involved in the destruction of neurons in people afflicted by strokes or neurodegenerative diseases such as Alzheimer's disease, Parkinson's disease, and amyotrophic lateral sclerosis (ALS). There is also evidence suggesting that ischemia can kill neurons by inducing apoptosis. It has been shown that neurons that are resistant to apoptosis are also resistant to ischemic damage, thus, inhibition of apoptosis may be a therapeutic strategy for the treatment of neurodegenerative or cardiovascular disorders, e.g., stroke.

Under normal physiological conditions, self-reactive immune cells may be induced to undergo apoptosis, thereby removing such self-reactive cells. A failure of the immune system to induce apoptosis in a self-reactive immune cell can lead to autoimmune disease. For example, autoimmune diseases such as rheumatoid arthritis, diabetes, and multiple sclerosis, result when a small percentage of T cells attack the body's own tissue.

There is a need in the art for methods of modulating cell death resulting from genotoxic insults. The present invention addresses this need, and provides related advantages as well.

SUMMARY OF THE INVENTION

The present invention provides methods for reducing DNA damage, resulting from a genotoxic insult, in a eukaryotic cell; and methods for modulating cell death in a eukaryotic cell. The methods generally comprise modulating a biological activity of DNA-PK in a cell. In some embodiments, the methods comprise contacting a eukaryotic cell with an immunomodulatory nucleic acid molecule that binds specifically to Ku protein, either alone or as part of the DNA-PK complex. These methods are useful for treating any disorder resulting from a genotoxic insult to a cell, e.g., necrosis, apoptosis, and disorders arising from necrosis and apoptosis. These methods are useful in modulating cell death in an individual, e.g., to treat various apoptosis-related and necrosis-related disorders. Accordingly, the invention further provides methods of treating a condition related to cell death in an individual. In one particular embodiment, cell death triggered by hypoxic or anoxic conditions is reduced. Accordingly, the invention further provides methods for reducing DNA damage mediated by hypoxic or anoxic conditions. These methods find use in treating a variety of conditions, including, e.g., ischemic heart disease.

The invention further provides methods of identifying agents which modulate a biological activity of DNA-PK. Agents modulate a biological activity of DNA-PK include DNA-PK antagonists and DNA-PK agonists. In some embodiments, agents are those which specifically bind the Ku polypeptide portion of the DNA-PK complex. In some embodiments, the screening methods are cell-based methods. In other embodiments, the screening methods are cell-free methods. In some of these embodiments, the methods involve an assay to determine whether a candidate agent is capable of competing with a known immunomodulatory polynucleotide for binding to Ku polypeptide.

The invention further provides agents identified by the screening methods of the invention, as well as compositions comprising the agents. Agents identified may enhance, inhibit, or mimic an activity of an immunomodulatory nucleic acid molecule. An identified agent may be useful in modulating an immune response in an individual. Antagonists and agonists of DNA-PK find use in a variety of methods, including methods of reducing DNA damage resulting from a genotoxic insult, methods of inducing apoptosis, and methods of inhibiting apoptosis. The invention further provides methods of modulating an immune response, generally comprising administering an identified agent to an individual. In some embodiments, methods of enhancing a Th1 response, and methods of reducing a Th2 response are provided.

These and other features of the invention will become apparent to those persons skilled in the art upon reading the details of the invention as more fully described below.

BRIEF DESCRIPTIONS OF THE DRAWINGS

FIGS. 1A–D depict various aspects of characterization of ISS-binding Ku antigen from mouse livers. FIG. 1A depicts the results of RT-PCR analysis to detect the presence of IL-6, IL-12, and GAPDH transcripts in mouse livers treated with double-stranded ISS, single-stranded ISS, or mutant ISS. FIG. 1B depicts the results showing identification of ISS-binding protein as Ku. FIGS. 1C and 1D depict results showing DNA binding specificity of Ku antigen for ds-ISS and ss-ISS, respectively.

FIGS. 2A–C depict results which show that Ku antigen is required for the induction of cytokines by ISS. BMDM from wild-type, Ku70$^{-/-}$ and Ku80$^{-/-}$ mice were treated with LPS, ISS, or mutant ISS for 24 hours, after which IL-6 (FIG. 2A) or IL-12 (FIG. 2B) protein levels were measured in culture supernatants. IL-6 and IL-12 mRNA levels were also measured by Northern blot analysis 6.5 hours after treatment of BMDM with ISS, as shown in FIG. 2C.

FIGS. 3A–D depict results that show that DNA-PKcs is required for the induction of IL-6 and IL-12 by ISS. BMDM from wild-type, or DNA-PKcs$^{-/-}$ were treated with ISS, mutant ISS, LPS, or were left untreated, for 24 hours, after which IL-6 (FIG. 3A) or IL-12 (FIG. 3B) protein levels were measured in culture supernatants. IL-6 and IL-12 mRNA levels were also measured by Northern blot analysis 6.5 hours after treatment of BMDM with ISS, as shown in FIG. 3C. FIG. 3D shows the results of in vivo analysis of the effect of ISS injected i.v., into wild-type or DNA-PKcs$^{-/-}$ mice on IL-6 and IL-12 expression in spleen and liver.

FIGS. 4E–H are graphs depicting results that show that DNA-PKcs is required for the induction of IL-6 and IL-12 by ISS. FIGS. 4E and 4F show the effect of wortmannin on IL-6 and IL-12 production, respectively.

FIGS. 4G and 4H show production of IL-6 and IL-12, respectively, in BMDM from ATM$^{-/-}$ mice treated with ISS, mutant ISS, LPS, or untreated.

FIGS. 5A–E depicts results that show involvement of IKK in NF-κB activation by ISS.

FIGS. 6A–C depicts results that show the role of DNA-PKcs in activation of IKK by ISS.

FIGS. 7A and B depict results showing that ISS activates DNA-PK in vitro and in vivo.

DETAILED DESCRIPTION OF THE INVENTION

Figure 2A:
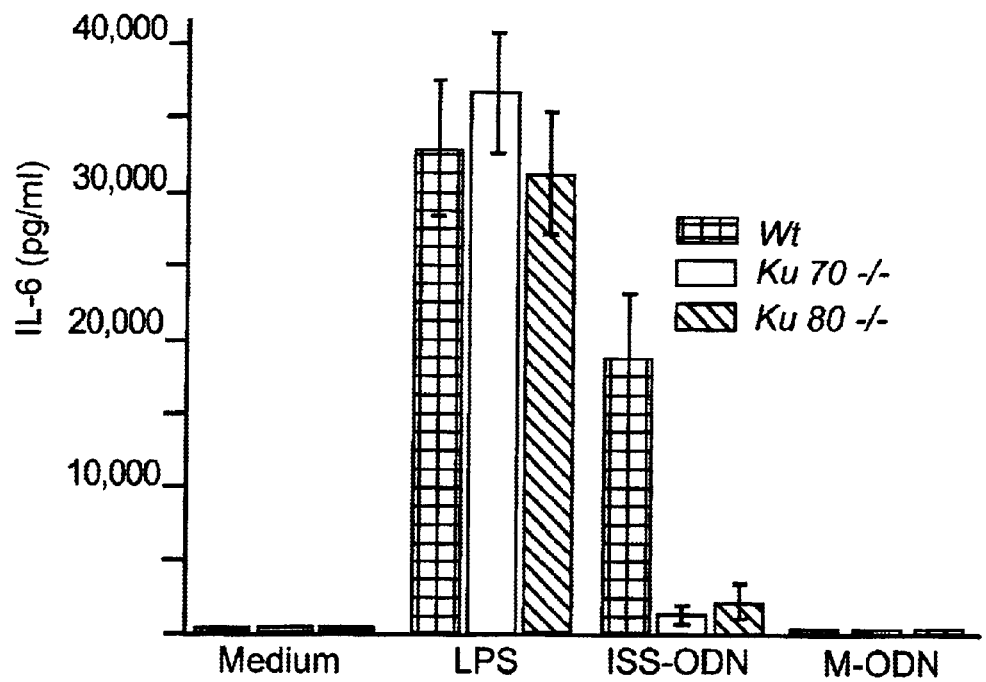

The present invention is based on the following unexpected observations: (1) nucleic acid molecules previously identified as modulating the immune response ("immunomodulatory nucleic acid molecule") bind to Ku antigen, resulting in activation of DNA-PKcs; (2) immunomodulatory nucleic acid molecules activate the anti-apoptotic PI3P-dependent kinase Akt; and (3) immunomodulatory nucleic acid molecules induce an anti-apoptotic response in eukaryotic cells. The present invention makes use of and extends these observations by providing methods of reducing DNA damage in a eukaryotic cell where the DNA damage is a result of a genotoxic insult; and methods of increasing or decreasing cell death in a eukaryotic cell. Such methods are useful for treating a variety of pathological conditions relating to cell death (e.g., conditions relating to necrosis and conditions relating to apoptosis), or lack thereof. The invention further provides methods for identifying agents that bind specifically to Ku antigen, and which therefore may be useful in methods to modulate an immune response, and in methods to modulate cell death.

Without wishing to be bound by theory, it is believed that immunostimulatory nucleic acid molecules mimic the signal delivered by DNA damage and activate one or more components of the molecular machinery, e.g., DNA-PK, which are involved in repairing DNA damage (e.g., DSB).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an immunomodulatory nucleic acid molecule" includes a plurality of such nucleic acid molecules and reference to "the agent" includes reference to one or more agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "a biological activity of DNA-PK," as used herein, refers to a biological activity of DNA-PK which, when modified, affects the activity of DNA-PK in repairing DNA damage in a eukaryotic cell. A biological activity of DNA-PK encompasses a biological activity of either of its components, e.g., Ku antigen and DNA-PKcs, separately or in complex with one another. Biological activities of DNA-PK include, but are not limited to, binding to double-strand breaks in DNA; Ku binding to DNA-PKcs; binding of DNA-PK or its components to other factors, such as immunomodulatory nucleic acid molecules, polypeptides, etc., which modulate DNA-PK activity in repairing DNA damage; and phosphorylation of factors, such as polypeptides, by DNA-PKcs.

The terms "Ku antigen," "Ku polypeptide," and "Ku protein," used interchangeably herein, refer to the heterodimeric Ku protein (comprising the Ku70 and Ku80 chains), the isolated Ku 70 chain, the isolated Ku 80 chain, and variants and fusion proteins of the foregoing. Ku antigen may be derived from any organism, including, but not limited to human, a murine, or other vertebrate. Ku antigen may be derived from a natural source, or may be completely or partially synthetic. The amino acid sequence of Ku antigen has been reported for mouse and human. These sequences may be found in the Swiss-Prot database under accession numbers P12956 and NP 001460 (human Ku 70); S25149 (mouse Ku 70); and P13010 and A32626 (human Ku 80). Ku antigen may have a wild-type or a variant amino acid sequence. Variants include Ku antigen comprising one or more truncations, internal deletions, substitutions, additions, or other modifications such as glycosylations, phosphorylations, acylations, etc. Variants further include fusion proteins comprising Ku antigen and a heterologous protein, including, but not limited to, an immunologically detectable protein, e.g., an epitope tag; a protein which directly provides a detectable signal, e.g., a green fluorescent protein; an enzyme which, upon action on a substrate, can yield a detectable product, e.g., alkaline phosphatase. Preferably, a Ku antigen or Ku antigen variant is biologically active. As used herein, "biologically active Ku antigen" is a Ku antigen which specifically binds an immunomodulatory nucleic acid molecule, and/or which activates DNA-PKcs activity.

The term "immunomodulatory," as used herein in reference to a nucleic acid molecule, refers to the ability of a nucleic acid molecule to modulate an immune response in a vertebrate host. "Immunomodulatory" includes "immunostimulatory" and "immunoinhibitory." Whether an immunomodulatory nucleic acid molecule is immunostimulatory or immunoinhibitory may be expressed in terms of the aspect of the immune response being modulated, e.g., relative enhancement, increase, or induction of a Th1 or a Th2 cell-mediated immune response. Modulation of an immune response includes, but is not limited to, enhancing or increasing a Th1 response, and/or decreasing or inhibiting a Th2 response, and/or decreasing or inhibiting a Th1 response.

The terms "oligonucleotide," "polynucleotide," and "nucleic acid molecule", used interchangeably herein, refer to a polymeric forms of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites, and/or phosphorothioates, and thus can be an oligodeoxynucleoside phosphoramidate or a mixed phosphoramidate-phosphodiester oligomer. Peyrottes et al. (1996) Nucl. Acids Res. 24:1841–1848; Chaturvedi et al. (1996) Nucl. Acids Res. 24:2318–2323. The polynucleotide may comprise one or more L-nucleosides. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

The terms "polypeptide," "peptide," and "protein", used interchangeably herein, refer to a polymeric form of amino acids of any length, which can include coded and non-coded amino acids, chemically or biochemically modified or derivatized amino acids, and polypeptides having modified peptide backbones. The term includes polypeptide chains modified or derivatized in any manner, including, but not limited to, glycosylation, formylation, cyclization, acetylation, phosphorylation, and the like. The term includes naturally-occurring peptides, synthetic peptides, and peptides comprising one or more amino acid analogs. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein the term "isolated" is meant to describe a polynucleotide, a polypeptide, an antibody, or a host cell that is in an environment different from that in which the polynucleotide, the polypeptide, the antibody, or the host cell naturally occurs. As used herein, the term "substantially purified" refers to a compound (e.g., either a polynucleotide or a polypeptide or an antibody) that is removed from its natural environment and is at least 60% free, preferably 75% free, and most preferably 90% free from other components with which it is naturally associated.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used herein, the term "DNA damage" includes, but is not limited to, single-strand breaks, double-strand breaks, alkali-labile sites, oxidative damage, DNA cross-linking, and incomplete excision repair sites.

As used herein, the term "cell death" refers to cell death arising from any cause, and includes necrosis, apoptosis, and a combination of necrosis and apoptosis.

As used herein, the terms "an cell death-related condition" and "a condition related to cell death," and "condition caused by cell death," are used interchangeably herein to refer to a condition (the term "condition" being used interchangeably herein with the terms "disease" and "disorder") associated with abnormally high rates (e.g., higher than physiologically normal in the absence of the condition) of cell death. It is also a condition which is amenable to treatment by inducing cell death, e.g., to reduce proliferation of an undesired cell.

The terms "genotoxic factor," and "genotoxic insult", used interchangeably herein, refer to any of a variety of environmental insults that result in DNA damage in a eukaryotic cell, e.g., may adversely affect the structure and/or integrity of DNA in a eukaryotic cell, and which thus may lead to cell death. Genotoxic factors include, but are not limited to, anoxia, hypoxia, ischemia, reperfusion injury, UV irradiation, gamma irradiation, DNA-damaging chemicals, and anti-cancer drugs that target DNA.

"Ischemia" is defined as an insufficient supply of blood to a specific organ or tissue. A consequence of decreased blood supply is an inadequate supply of oxygen to the organ or tissue (hypoxia). Prolonged hypoxia may result in injury to the affected organ or tissue. "Anoxia" refers to a virtually complete absence of oxygen in the organ or tissue, which, if prolonged, may result in death of the organ or tissue.

"Hypoxia" and "anoxia" refer to a reduction of oxygen supply to a tissue below physiological levels. A "hypoxic condition" refers to a condition under which a particular organ or tissue receives an inadequate supply of oxygen. An "anoxic condition" refers to a condition under which the supply of oxygen to a particular organ or tissue is cut off.

"Reperfusion" refers to the resumption of blood flow in a tissue following a period of ischemia.

"Ischemic injury" refers to cellular and/or molecular damage to an organ or tissue as a result of a period of ischemia and/or ischemia followed by reperfusion.

The terms "preventing," "reducing," and "inhibiting" are used interchangeably herein. In the context of modulating cell death, these terms refer to a reduction in cell death or a prolongation in the survival time of the cell. They also are intended to include a diminution in the appearance or a delay in the appearance of morphological and/or biochemical changes normally associated with apoptosis and/or necrosis. Thus a reduction in cell death leads to increased survival time and/or survival rate of a cell or population of cells which, absent the use of a method to reduce cell death, would normally be expected to die.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "cancer", "neoplasm", "tumor", and "carcinoma", are used interchangeably herein to refer to cells which exhibit relatively autonomous growth, such that they exhibit an aberrant growth phenotype characterized by a significant loss of control of cell proliferation. Cancerous cells can be benign or malignant.

By "individual" or "host" or "subject" or "patient" is meant any mammalian subject for whom diagnosis, treatment, or therapy is desired, particularly humans. Other subjects may include cattle, dogs, cats, pigs, rabbits, rats, mice, horses, and so on.

Methods of the Invention

The present invention provides methods for modulating cell death in a eukaryotic cell; and methods for reducing DNA damage due to a genotoxic insult in a eukaryotic cell. The methods generally comprise contacting the cell with an agent that modulates a biological activity of DNA-PK. In some embodiments, the methods provide for decreasing cell death in a eukaryotic cell by activating DNA-PKcs in the cell. In other embodiments, the methods provide for increasing cell death in a eukaryotic cell by decreasing DNA-PKcs activity in the cell. The invention further provides methods of treating a cell death-related condition in an individual.

In some embodiments, the methods comprise contacting a cell with an immunomodulatory nucleic acid molecule. Immunomodulatory nucleic acid molecules suitable for use in these methods are described in more detail below. Immunomodulatory nucleic acid molecules can bind to Ku polypeptide and activate DNA-PKcs activity in a cell.

In some embodiments, methods are provided for reducing DNA damage resulting from exposure to a genotoxic factor in a eukaryotic cell in response to a genotoxic factor. The methods generally comprise contacting the cell with an agent that modulates a biological activity of DNA-PK, as described above. In these embodiments, an "effective amount" of an agent is an amount effective to decrease the DNA damage by at least about 10%, at least about 20%, at least about 25%, at least about 30%, at least about 40%, at least about 50%, at least about 60%, at least about 70%, at least about 80%, at least about 90%, or up to 100%, in the cell, when compared to DNA damage in a cell exposed to the genotoxic factor but not contacted with the agent.

The methods can be used in vitro (e.g., in a screening assay), in vivo (e.g., in therapeutic methods), or ex vivo (e.g., in therapeutic methods such as reducing cell death in an organ or tissue or cells to be transplanted). For in vivo use, a formulation comprising an effective amount of an agent that modulates a biological activity of DNA-PK in a eukaryotic cell is administered to an individual in need thereof. An "effective amount" of an agent that decreases a biological activity of DNA-PK activity in a eukaryotic cell is an amount is an amount effective to decrease the DNA-PK biological activity by at least about 10%, at least about 20%, at least about 25%, at least about 30%, at least about 40%, at least about 50%, at least about 60%, at least about 70%, at least about 80%, at least about 90%, or up to 100%, in the cell. An "effective amount" of an agent that increases a biological activity of DNA-PK in a eukaryotic cell is an amount is an amount effective to increase the biological activity of DNA-PK by at least about 10%, at least about 25%, at least about 50%, at least about 75%, at least about 100% (or two-fold), at least about 5-fold, at least about 10-fold, at least about 25-fold, or at least about 50-fold or more, in the cell.

Any biological activity of DNA-PK can be detected, including, but not limited to, (1) enzymatic activity of DNA-PK in phosphorylating a substrate polypeptide; (2) the level of cell death in a cell population as an indication of the level of DNA-PK activity; (3) measuring Ku binding to DNA-PKcs; (4) binding of an immunomodulatory nucleic acid molecule to Ku; (5) activity of a polypeptide in the pathway of DNA-PK activation, e.g., Akt-1; and (6) binding of a polypeptide (e.g., replication protein A, "RPA") to the DNA-PK complex. "Detecting," as used herein, encompasses determining the presence or absence of a biological activity; determining a relative increase or decrease in a biological activity; and measuring quantitatively the level of a biological activity. Accordingly, "detecting" encompasses both quantitative and qualitative determinations.

DNA-PK enzymatic activity can be detected using any method known in the art. DNA-PK activity can be measured in a reaction mixture comprising linear, double-stranded DNA, a suitable polypeptide or peptide substrate, $Mg^{2+}$ ions, ATP, and gamma-labeled ATP, e.g., $[\gamma^{-32}P]$-labeled ATP. Methods for measuring DNA-PK activity have been described in the art. See, e.g., Basu et al. (1998) *Biochem. Biophys. Res. Comm.* 247:79–83, the contents of which is incorporated herein by reference for their teaching of assays for DNA-PK activity. In general, a polypeptide substrate for DNA-PK comprises a minimal target sequence for phosphorylation by DNA-PK consists of a serine or threonine residue adjacent to a glutamine (on either side) with no nearby basic amino acids. An example of a peptide substrate specific for DNA-PK has the following amino acid sequence: Glu-Pro-Pro-Leu-Ser-Gln-Glu-Ala-Phe-Ala-Asp-Leu-Trp-Lys-Lys. Kits for assaying DNA-PK activity are commercially available from, e.g., Promega. Reaction products are analyzed for incorporation of labeled phosphate into the peptide or polypeptide substrate, using standard techniques. As one example, reaction products are spotted onto phosphocellulose paper; dried; washed to remove unincorporated $[\gamma^{-32}P]$-ATP; dried; and spots cut out and counted in a scintillation counter.

DNA damage can be detected using any known method, including, but not limited to, a Comet assay (commercially available from Trevigen, Inc.), which is based on alkaline lysis of labile DNA at sites of damage; and immunological assays using antibodies specific for aberrant DNA structures, e.g., 8-OHdG.

Cell death can be measured using any known method, and is generally measured using any of a variety of known methods for measuring cell viability. Such assays are generally based on entry into the cell of a detectable compound (or a compound that becomes detectable upon interacting with, or being acted on by, an intracellular component) that would normally be excluded from a normal, living cell by its intact cell membrane. Such compounds include substrates for intracellular enzymes, including, but not limited to, a fluorescent substrate for esterase; dyes that are excluded from living cell, including, but not limited to, trypan blue; and DNA-binding compounds, including, but not limited to, an ethidium compound such as ethidium bromide and ethidium homodimer, and propidium iodide.

Apoptosis can be assayed using any known method. Assays can be conducted on cell populations or an individual cell, and include morphological assays and biochemical assays. A non-limiting example of a method of determining the level of apoptosis in a cell population is TUNEL (TdT-mediated dUTP nick-end labeling) labeling of the 3'-OH free end of DNA fragments produced during apoptosis (Gavrieli et al. (1992) *J. Cell Biol.* 119:493). The TUNEL method consists of catalytically adding a nucleotide, which has been conjugated to a chromogen system or a to a fluorescent tag, to the 3'-OH end of the 180-bp (base pair) oligomer DNA fragments in order to detect the fragments. The presence of a DNA ladder of 180-bp oligomers is indicative of apoptosis. Procedures to detect cell death based on the TUNEL method are available commercially, e.g., from Boehringer Mannheim (Cell Death Kit) and Oncor (Apoptag Plus). Another marker that is currently available is annexin, sold under the trademark APOPTEST™. This marker is used in the "Apoptosis Detection Kit," which is also commercially available, e.g., from R&D Systems. During apoptosis, a cell membrane's phospholipid asymmetry changes such that the phospholipids are exposed on the outer membrane. Annexins are a homologous group of proteins that bind phospholipids in the presence of calcium. A second reagent, propidium iodide (PI), is a DNA binding fluorochrome. When a cell population is exposed to both reagents, apoptotic cells stain positive for annexin and negative for PI, necrotic cells stain positive for both, live cells stain negative for both. Other methods of testing for apoptosis are known in the art and can be used, including, e.g., the method disclosed in U.S. Pat. No. 6,048,703.

Binding of Ku polypeptide to DNA-PKcs can be detected by standard protein—protein interaction assays, e.g., immunological assays such as co-precipitation of DNA-PKcs with an antibody to Ku polypeptide, and the like.

In some embodiments, an immunomodulatory nucleic acid molecule activates a kinase activity of Akt-1. Akt-1 (also known as PKB-α and RAC-PK-α) is a member of the AKT/PKB family of serine/threonine kinases and has been shown to be involved in a diverse set of signaling pathways. Akt-1, like other members of the AKT/PKB family is located in the cytosol of unstimulated cells and translocates to the cell membrane following stimulation. Akt-1 has been cloned and sequenced. Bellacosa et al. (1991) *Science* 254:274–277; Coffer and Woodgett (1991) *Eur. J. Biochem.* 201:475–481; Jones et al. (1991) *Cell Regul.* 2: 1001–1009. Akt-1 is a phosphatidylinositol-3,4,5-trisphosphate (PIP3)-dependent anti-apoptotic kinase, and plays a role in the prevention of "programmed cell death" or apoptosis. Phosphatidylinositol 3-kinase (PI3-K) phosphorylates Akt, which phosphorylation serves to activate the anti-apoptotic activity of Akt. It has been demonstrated that Akt-1 provides a survival signal to cells protecting them from a number of agents including UV radiation, withdrawal of IGF1 from neuronal cells, detachment from the extracellular matrix, stress and heat shock. Dudek et al. (1997) *Science* 275:661–665; and Alessi and Cohen (1998) *Curr. Opin. Genet. Dev.* 8:55–62. Assays for Akt-1 kinase activity are known in the art and have been amply described, e.g., in the above-mentioned publications. In general, a substrate for Akt-1 and [γ-$^{32}$P]-ATP are provided in a reaction mixture, and phosphorylation of the substrate is monitored using conventional assays.

Methods of detecting binding of DNA-PK to other polypeptides such as RPA are known in the art, and any such method can be used in conjunction with the methods of the present invention.

Immunomodulatory Nucleic Acid Molecules Suitable for use in the Methods of the Invention The term "polynucleotide," as used in the context of immunomodulatory nucleic acid molecules, is a polynucleotide as defined above, and encompasses, inter alia, single- and double-stranded oligonucleotides (including deoxyribonucleotides, ribonucleotides, or both), modified oligonucleotides, and oligonucleosides, alone or as part of a larger nucleic acid construct, or as part of a conjugate with a non-nucleic acid molecule such as a polypeptides. Thus immunomodulatory nucleic acid molecules may be, for example, single-stranded DNA (ssDNA), double-stranded DNA (dsDNA), single-stranded RNA (ssRNA) or double-stranded RNA (dsRNA). Immunomodulatory nucleic acid molecules also encompasses crude, detoxified bacterial (e.g., mycobacterial) RNA or DNA, as well as enriched plasmids enriched for immunomodulatory nucleic acid molecules. In some embodiments, an "immunomodulatory nucleic acid molecules-enriched plasmid" refers to a linear or circular plasmid that comprises or is engineered to comprise a greater number of CpG motifs than normally found in mammalian DNA. Exemplary immunomodulatory nucleic acid molecules-enriched plasmids are described in, for example, Roman et al. (1997) *Nat. Med.* 3(8):849–54. Modifications of oligonucleotides include, but are not limited to, modifications of the 3'OH or 5'OH group, modifications of the nucleotide base, modifications of the sugar component, and modifications of the phosphate group.

An immunomodulatory nucleic acid molecule may comprise at least one nucleoside comprising an L-sugar. The L-sugar may be deoxyribose, ribose, pentose, deoxypentose, hexose, deoxyhexose, glucose, galactose, arabinose, xylose, lyxose, or a sugar "analog" cyclopentyl group. The L-sugar may be in pyranosyl or furanosyl form.

An immunomodulatory nucleic acid molecule may comprise a modified cytosine, e.g., as described in PCT Publication No. WO 99/62923.

Immunomodulatory nucleic acid molecules generally do not provide for, nor is there any requirement that they provide for, expression of any amino acid sequence encoded by the polynucleotide, and thus the sequence of a immunomodulatory nucleic acid molecule may be, and generally is, non-coding. Immunomodulatory nucleic acid molecules may comprise a linear double or single-stranded molecule, a circular molecule, or can comprise both linear and circular segments. Immunomodulatory nucleic acid molecules may be single-stranded, or may be completely or partially double-stranded.

In some embodiments, an immunomodulatory nucleic acid molecule is an oligonucleotide, e.g., consists of a sequence of from about 6 to about 200, from about 10 to about 100, from about 12 to about 50, or from about 15 to about 25, nucleotides in length.

In other embodiments, an immunomodulatory nucleic acid molecule is part of a larger nucleotide construct (e.g., a plasmid vector, a viral vector, or other such construct). A wide variety of plasmid and viral vector are known in the art, and need not be elaborated upon here. A large number of such vectors have been described in various publications, including, e.g., *Current Protocols in Molecular Biology*, (F. M. Ausubel, et al., Eds. 1987, and updates). Many vectors are commercially available.

Immunomodulatory Nucleic Acid Molecules Comprising a CpG Motif

In some embodiments, the immunomodulatory nucleic acid molecules used in the invention comprise at least one unmethylated CpG motif. In general, these immunomodulatory nucleic acid molecules increase a Th1 response in an individual. The relative position of any CpG sequence in a polynucleotide having immunomodulatory activity in certain mammalian species (e.g., rodents) is 5'-CG-3' (i.e., the C is in the 5' position with respect to the G in the 3' position). Immunomodulatory nucleic acid molecules can be conveniently obtained by substituting the cytosine in the CpG dinucleotide with another nucleotide, particularly a purine nucleotide. A substitution of particular interest is with a guanine to form an immunomodulatory nucleic acid molecule comprising a GpG dinucleotide.

Exemplary immunomodulatory nucleic acid molecules useful in the invention include, but are not necessarily limited to, those comprising the following core nucleotide sequences: 1) hexameric core sequences comprising "CpG" motifs or comprising XpY motifs, where X cannot be C if Y is G and vice-versa; 2) octameric core sequences comprising "CpG" motifs or comprising XpY motifs, where X cannot be C if Y is G and vice-versa; and 3) inosine and/or uracil substitutions for nucleotides in the foregoing hexameric or octameric sequences for use as RNA immunomodulatory nucleic acid molecule (e.g., substituting uracil for thymine and/or substituting inosine for a purine nucleotide). As used herein, "core sequence" in the context of an immunomodulatory nucleic acid molecule refers to a minimal sequence that provides for, facilitates, or confers the immunomodulatory activity of the nucleic acid molecule.

Exemplary consensus CpG motifs of immunomodulatory nucleic acid molecules useful in the invention include, but are not necessarily limited to:

5'-Purine-Purine-[C]-[G]-Pyrimidine-Pyrimidine-3', in which the immunomodulatory nucleic acid molecule comprises a CpG motif flanked by at least two purine nucleotides (e.g., GG, GA, AG, AA, II, etc.,) and at least two pyrimidine nucleotides (CC, TT, CT, TC, UU, etc.);
5'-Purine-TCG-Pyrimidine-Pyrimidine-3';
5'-[TCG]$_n$-3', where n is any integer that is 1 or greater, e.g., to provide a poly-TCG immunomodulatory nucleic acid molecule (e.g., where n=3, the polynucleotide comprises the sequence 5'-TCGTCGTCG-3');
5'-Purine-Purine-CG-Pyrimidine-Pyrimidine-CG-3';
5'-Purine-TCG-Pyrimidine-Pyrimidine-CG-3'; and
5'-Purine-Purine-CG-Pyrimidine-Pyrimidine-CG-3'.

The core structure of immunomodulatory nucleic acid molecules useful in the invention may be flanked upstream and/or downstream by any number or composition of nucleotides or nucleosides. In some embodiments, the core sequence of immunomodulatory nucleic acid molecules are at least 6 bases or 8 bases in length, and the complete immunomodulatory nucleic acid molecules (core sequences plus flanking sequences 5', 3' or both) are usually between 6 bases or 8 bases, and up to about 200 bases in length to enhance uptake of the immunomodulatory nucleic acid molecules. Those of ordinary skill in the art will be familiar with, or can readily identify, reported nucleotide sequences of known immunomodulatory nucleic acid molecules for reference in preparing immunomodulatory nucleic acid molecules, see, e.g., Yamamoto, et al., (1992) *Microbiol. Immunol.*, 36:983; Ballas, et al., (1996) *J. Immunol.*, 157:1840; Kliniman, et al., (1997) *J. Immunol.*, 158:3635; Sato, et al., (1996) *Science*, 273:352, each of which are incorporated herein by reference. In addition, immunomodulatory nucleic acid molecules useful in the invention have been described in, for example, PCT publication nos. WO 98/16427, WO 98/55495, and WO 99/11275.

Exemplary DNA-based immunomodulatory nucleic acid molecules useful in the invention include, but are not necessarily limited to, polynucleotides comprising the following nucleotide sequences:

```
AACGCC, AACGCT, AACGTC, AACGTT;
AGCGCC, AGCGCT, AGCGTC, AGCGTT;
GACGCC, GACGCT, GACGTC, GACGTT;
GGCGCC, GGCGCT, GGCGTC, GGCGTT;
```

-continued

```
ATCGCC, ATCGCT, ATCGTC, ATCGTT;
GTCGCC, GTCGCT, GTCGTC, GTCGTT; and
TCGTCG, and TCGTCGTCG.
```

Octameric sequences are generally the above-mentioned hexameric sequences, with an additional 3' CG. Exemplary DNA-based immunomodulatory nucleic acid molecules useful in the invention include, but are not necessarily limited to, polynucleotides comprising the following octameric nucleotide sequences:

```
AACGCCCG, AACGCTCG, AACGTCCG, AACGTTCG;
AGCGCCCG, AGCGCTCG, AGCGTCCG, AGCGTTCG;
GACGCCCG, GACGCTCG, GACGTCCG, GACGTTCG;
GGCGCCCG, GGCGCTCG, GGCGTCCG, GGCGTTCG;
ATCGCCCG, ATCGCTCG, ATCGTCCG, ATCGTTCG;
GTCGCCCG, GTCGCTCG, GTCGTCCG, GTCGTTCG; and
GTCGTTCG.
```

Immunomodulatory nucleic acid molecules useful in the invention can comprise one or more of any of the above CpG motifs. For example, immunomodulatory nucleic acid molecules useful in the invention can comprise a single instance or multiple instances (e.g., 2, 3, 5 or more) of the same CpG motif. Alternatively, the immunomodulatory nucleic acid molecules can comprises multiple CpG motifs (e.g., 2, 3, 5 or more) where at least two of the multiple CpG motifs have different consensus sequences, or where all CpG motifs in the immunomodulatory nucleic acid molecules have different consensus sequences.

Immunomodulatory nucleic acid molecules useful in the invention may or may not include palindromic regions. If present, a palindrome may extend only to a CpG motif, if present, in the core hexamer or octamer sequence, or may encompass more of the hexamer or octamer sequence as well as flanking nucleotide sequences.

Modifications

Immunomodulatory nucleic acid molecules can be modified in a variety of ways. For example, an immunomodulatory nucleic acid molecules can comprise backbone phosphate group modifications (e.g., methylphosphonate, phosphorothioate, phosphoroamidate and phosphorodithioate internucleotide linkages), which modifications can, for example, confer inherent anti-microbial activity on the immunomodulatory nucleic acid molecule and enhance their stability in vivo, making them particularly useful in therapeutic applications. A particularly useful phosphate group modification is the conversion to the phosphorothioate or phosphorodithioate forms of an immunomodulatory nucleic acid molecule. In addition to their potentially anti-microbial properties, phosphorothioates and phosphorodithioates are more resistant to degradation in vivo than their unmodified oligonucleotide counterparts, increasing the half-lives of the immunomodulatory nucleic acid molecules and making them more available to the subject being treated.

Other modified immunomodulatory nucleic acid molecules include immunomodulatory nucleic acid molecules having modifications at the 5' end, the 3' end, or both the 5' and 3' ends. For example, the 5' and/or 3' end can be covalently or non-covalently conjugated to a molecule (either nucleic acid, non-nucleic acid, or both) to, for example, increase the bio-availability of the immunomodulatory nucleic acid molecules, increase the efficiency of uptake where desirable, facilitate delivery to cells of interest, and the like. Exemplary molecules for conjugation to the immunomodulatory nucleic acid molecules include, but are not necessarily limited to, cholesterol, phospholipids, fatty acids, sterols, oligosaccharides, polypeptides (e.g., immunoglobulins), peptides, antigens (e.g., peptides, small molecules, etc.), linear or circular nucleic acid molecules (e.g., a plasmid), and the like. Additional immunomodulatory nucleic acid conjugates, and methods for making same, are known in the art and described in, for example, WO 98/16427 and WO 98/55495. Thus, the term "immunomodulatory nucleic acid molecule" includes conjugates comprising an immunomodulatory nucleic acid molecule.

Formulations

In general, immunomodulatory nucleic acid molecules are prepared in a pharmaceutically acceptable composition for delivery to a host. Pharmaceutically acceptable carriers preferred for use with the immunomodulatory nucleic acid molecules in carrying out treatment methods of the invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising a immunomodulatory nucleic acid molecule may also be lyophilized using means well known in the art, for subsequent reconstitution and use according to the invention. Also contemplated are microencapsulation carriers, such as liposomes, microspheres, and the like.

In general, the pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. Preservatives and other additives may also be present such as, for example, antimicrobials, antioxidants, chelating agents, and inert gases and the like. In one embodiment, as discussed above, the immunomodulatory nucleic acid molecule formulation comprises an additional anti-mycobacterial agent.

Immunomodulatory nucleic acid molecules can be administered in the absence of an amount of agents or compounds sufficient to facilitate uptake by target cells (e.g., as a "naked" polynucleotide, e.g., a polynucleotide that is not encapsulated by a viral particle, or a nucleic acid molecule not administered with an adjuvant). Immunomodulatory nucleic acid molecules can be administered in microencapsulated form, e.g., in microspheres, and the like. Immunomodulatory nucleic acid molecules can be administered with compounds that facilitate uptake of immunomodulatory nucleic acid molecules by target cells (e.g., by macrophages) or otherwise enhance transport of an immunomodulatory nucleic acid molecule to a treatment site for action. Absorption promoters, detergents and chemical irritants (e.g., keratinolytic agents) can enhance transmission of an immunomodulatory nucleic acid molecule composition into a target tissue (e.g., through the skin). For general principles regarding absorption promoters and detergents which have been used with success in mucosal delivery of organic and peptide-based drugs, see, e.g., Chien, *Novel Drug Delivery Systems*, Ch. 4 (Marcel Dekker, 1992). Examples of suitable nasal absorption promoters in particular are set forth at Chien, supra at Ch. 5, Tables 2 and 3; milder agents are preferred. Suitable agents for use in the method of this invention for mucosal/nasal delivery are also described in Chang, et al., *Nasal Drug Delivery*, "Treatise on Controlled Drug Delivery", Ch. 9 and Tables 3–4B thereof, (Marcel Dekker, 1992). Suitable agents which are known to enhance absorption of drugs through skin are described in Sloan, Use of Solubility Parameters from Regular Solution Theory to Describe Partitioning-Driven Processes, Ch. 5, "Prodrugs: Topical and Ocular Drug Delivery" (Marcel Dekker, 1992), and at places elsewhere in the text. All of these references are incorporated herein for the sole purpose of illustrating the level of knowledge and skill in the art concerning drug delivery techniques.

A colloidal dispersion system may be used for targeted delivery of the immunomodulatory nucleic acid molecules to specific tissue. Colloidal dispersion systems include macromolecule complexes, nanocapsules, microspheres, beads, and lipid-based systems including oil-in-water emulsions, micelles, mixed micelles, and liposomes.

Liposomes are artificial membrane vesicles which are useful as delivery vehicles in vitro and in vivo. It has been shown that large unilamellar vesicles (LUV), which range in size from 0.2–4.0 Fm can encapsulate a substantial percentage of an aqueous buffer comprising large macromolecules. RNA and DNA can be encapsulated within the aqueous interior and be delivered to cells in a biologically active form (Fraley, et al, (1981) *Trends Biochem. Sci.*, 6:77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

Where desired, targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various well known linking groups can be used for joining the lipid chains to the targeting ligand (see, e.g., Yanagawa, et al., (1988) *Nuc. Acids Symp. Ser.*, 19:189; Grabarek, et al., (1990) *Anal. Biochem.* 185:131; Staros et al. (1986) *Anal. Biochem.* 156:220 and Boujrad, et al., (1993) *Proc. Natl. Acad. Sci. USA*, 90:5728). Targeted delivery of immunomodulatory nucleic acid molecules can also be achieved by conjugation of the immunostimulatory nucleic acid molecules to a the surface of viral and non-viral recombinant expression vectors, to an antigen or other ligand, to a monoclonal antibody or to any molecule which has the desired binding specificity.

Routes of Administration

Immunomodulatory nucleic acid molecules are administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the immunomodulatory nucleic acid and/or the desired effect on the immune response. The immunomodulatory nucleic acid composition can be administered in a single dose or in multiple doses, and may encompass administration of booster doses, to elicit and/or maintain the desired effect on the immune response.

Immunomodulatory nucleic acid molecules can be administered to a host using any available conventional methods and routes suitable for delivery of conventional drugs, including systemic or localized routes. In general, routes of administration contemplated by the invention include, but are not necessarily limited to, enteral, parenteral, or inhalational routes. Inhalational routes may be preferred in cases of pulmonary involvement, particularly in view of the activity of certain immunomodulatory nucleic acid molecules as a mucosal adjuvant.

Inhalational routes of administration (e.g., intranasal, intrapulmonary, and the like) are particularly useful in stimulating an immune response for prevention or treatment of infections of the respiratory tract. Such means include inhalation of aerosol suspensions or insufflation of the polynucleotide compositions of the invention. Nebulizer devices, metered dose inhalers, and the like suitable for delivery of polynucleotide compositions to the nasal mucosa, trachea and bronchioli are well-known in the art and will therefore not be described in detail here. For general review in regard to intranasal drug delivery, see, e.g., Chien, *Novel Drug Delivery Systems*, Ch. 5 (Marcel Dekker, 1992).

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of immunomodulatory nucleic acid molecules. Where systemic delivery is desired, administration typically involves invasive or systemically absorbed topical or mucosal administration of pharmaceutical preparations.

Immunomodulatory nucleic acid molecules can also be delivered to the subject by enteral administration. Enteral routes of administration include, but are not necessarily limited to, oral and rectal (e.g., using a suppository) delivery.

Methods of administration of immunomodulatory nucleic acid molecules through the skin or mucosa include, but are not necessarily limited to, topical application of a suitable pharmaceutical preparation, transdermal transmission, injection and epidermal administration. For transdermal transmission, absorption promoters or iontophoresis are suitable methods. For review regarding such methods, those of ordinary skill in the art may wish to consult Chien, supra at Ch. 7. Iontophoretic transmission may be accomplished using commercially available "patches" which deliver their product continuously via electric pulses through unbroken skin for periods of several days or more. An exemplary patch product for use in this method is the LECTRO PATCH™ (manufactured by General Medical Company, Los Angeles, Calif.) which electronically maintains reservoir electrodes at neutral pH and can be adapted to provide dosages of differing concentrations, to dose continuously and/or to dose periodically.

Epidermal administration can be accomplished by mechanically or chemically irritating the outermost layer of the epidermis sufficiently to provoke an immune response to the irritant. An exemplary device for use in epidermal administration employs a multiplicity of very narrow diameter, short tynes which can be used to scratch immunomodulatory nucleic acid molecules coated onto the tynes into the skin. The device included in the MONO-VACC™ tuberculin test (manufactured by Pasteur Merieux, Lyon, France) is suitable for use in epidermal administration of immunostimulatory nucleic acid molecules.

The invention also contemplates opthalmic administration of immunomodulatory nucleic acid molecules, which generally involves invasive or topical application of a pharmaceutical preparation to the eye. Eye drops, topical creams and injectable liquids are all examples of suitable formulations for delivering drugs to the eye.

Dosages

Although the dosage used will vary depending on the clinical goals to be achieved, a suitable dosage range is one which provides up to about 1 µg, about 1,000 µg, about 10,000 µg, about 20,000 µg, about 30,000 µg, about 40,000 µg, or about 50,000 µg of immunomodulatory nucleic acid molecule can be administered in a single dose. Alternatively, a target dosage of immunomodulatory nucleic acid molecule can be considered to be about 1–10 µM in a sample of host blood drawn within the first 24–48 hours after administration of immunomodulatory nucleic acid molecules. Based on current studies, immunomodulatory nucleic acid molecules are believed to have little or no toxicity at these dosage levels.

It should be noted that the activity of an immunomodulatory nucleic acid molecules is generally dose-dependent. Therefore, to increase immunomodulatory nucleic acid molecules potency by a magnitude of two, each single dose is doubled in concentration. Increased dosages may be needed to achieve the desired therapeutic goal. The invention thus contemplates administration of "booster" doses to provide and maintain a desired immune response. For example, immunomodulatory nucleic acid molecules may be administered at intervals ranging from at least every two weeks to every four weeks (e.g., monthly intervals) (e.g., every four weeks).

Cell Death-Related Disorders which are Amenable to Treatment

Cell death-related indications which can be treated using the methods of the invention for reducing cell death in a eukaryotic cell, include, but are not limited to, cell death associated with Alzheimer's disease, Parkinson's disease, rheumatoid arthritis, septic shock, sepsis, stroke, central nervous system inflammation, osteoporosis, ischemia, reperfusion injury, cell death associated with cardiovascular disease, polycystic kidney disease, cell death of endothelial cells in cardiovascular disease, degenerative liver disease, multiple sclerosis, amyotropic lateral sclerosis, cerebellar degeneration, ischemic injury, cerebral infarction, myocardial infarction, acquired immunodeficiency syndrome (AIDS), myelodysplastic syndromes, aplastic anemia, male pattern baldness, and head injury damage. Also included are conditions in which DNA damage to a cell is induced by, e.g., irradiation, radiomimetic drugs, and the like. Also included are any hypoxic or anoxic conditions, e.g., conditions relating to or resulting from ischemia, myocardial infarction, cerebral infarction, stroke, bypass heart surgery, organ transplantation, neuronal damage, and the like.

Cell death-related indications which can be treated using methods of the invention for activating cell death include, but are not limited to, undesired, excessive, or uncontrolled cellular proliferation, including, for example, neoplastic cells; as well as any undesired cell or cell type in which induction of cell death is desired, e.g., virus-infected cells and self-reactive immune cells. The methods may be used to treat follicular lymphomas, carcinomas associated with p53 mutations; autoimmune disorders, such as, for example, systemic lupus erythematosus (SLE), immune-mediated glomerulonephritis; hormone-dependent tumors, such as, for example, breast cancer, prostate cancer and ovary cancer; and viral infections, such as, for example, herpesviruses, poxviruses and adenoviruses.

Subjects to be treated according to the methods of the invention include any individual having any of the above-mentioned disorders. Further included are individuals who are at risk of developing any of the above-mentioned disorders, including, but not limited to, an individual who has suffered a myocardial infarction, and is therefore at risk for experiencing a subsequent myocardial infarction; an individual who has undergone organ or tissue transplantation; an individual who has had a stroke and is at risk for having a subsequent stroke; and an individual at risk of developing an autoimmune disorder due to genetic predisposition, or due to the appearance of early symptoms of autoimmune disorder.

Methods of Identifying an Agent that Modulate a Biological Activity of DNA-PK The present invention provides methods of identifying agents which modulate a biological activity of DNA-PK ("screening methods"). In some embodiments, the screening methods are cell-based methods. In other embodiments, the screening methods are cell-free methods. The term "modulate" encompasses an increase or a decrease in the detected DNA-PK biological activity when compared to a suitable control.

The methods generally comprise:

a) contacting a substance to be tested with a sample comprising DNA-PK, forming a test sample; and
b) detecting a biological activity of the DNA-PK in the test sample as compared to a control sample lacking the test agent.

An increase or a decrease in the biological activity of the DNA-PK indicates that the agent modulates a biological activity of the DNA-PK polypeptide.

Any biological activity of DNA-PK can be detected, including, but not limited to, (1) enzymatic activity of DNA-PK in phosphorylating a substrate polypeptide; (2) the level of cell death in a cell population as an indication of the level of DNA-PK activity; (3) Ku binding to DNA-PKcs; (4) binding of an immunomodulatory nucleic acid molecule to Ku; (5) activity of a polypeptide in the pathway of DNA-PK activition, e.g., Akt-1; and (6) binding of a polypeptide (e.g., replication protein A, "RPA") to the DNA-PK complex. "Detecting," as used herein, refers to determining the presence or absence of a biological activity; determining a relative increase or decrease in a biological activity; and measuring quantitatively the level of a biological activity.

In some embodiments, a detected biological activity of a DNA-PK is binding between the Ku polypeptide and the immunomodulatory nucleic acid molecule, wherein an increase or a decrease in binding activity in comparison to Ku binding activity in a suitable control is an indication that the substance modulates a biological activity of the Ku polypeptide.

In these embodiments, the methods comprise:

a) contacting a substance to be tested with a sample comprising DNA-PK and an immunomodulatory nucleic acid molecule, thereby forming a test sample; and
b) detecting the effect, if any, on a biological activity of DNA-PK in the test sample as compared to a control sample lacking the test agent.

In other embodiments, a detected biological activity of a DNA-PK is activation of DNA-PKcs activity. The readout may be direct measurement of DNA-PKcs activity (as described above); production of IL-6 or IL-12 (as measured by a polymerase chain reaction, e.g., for measuring IL-6 or IL-12 mRNA levels; or ELISA, for measuring IL-6, TNF-α, or IL-12 protein levels); or any other measurement, direct or indirect, of a DNA-PK biological activity.

In other embodiments, a detected biological activity of DNA-PK is binding of DNA-PK with other polypeptides such as replication protein A, heat shock factor-1, and any other polypeptide to which DNA-PK (or a component thereof) is known to bind. DNA-PK-interacting polypeptides include, but are not limited to, replication protein A (RPA), a heterotrimeric single-stranded DNA-binding protein (Zou and Stillman (2999) *Mol. Cell. Biol.* 20:3086–3096; and Shao et al. (1999) *EMBO J.* 18:1397–1406; and heat shock factor-1 (HSF-1) (Morano and Thiele (1999) *Gene Expression* 7:271–282; and Nueda et al. (1999) *J. Biol. Chem.* 274:14988–14996). Binding of DNA-PK to a DNA-PK-interacting polypeptide can be measured using any method known in the art to measure protein—protein interactions, including, but not limited to, protein interactive trapping assays, and immunological assays (e.g., using an antibody to one component to immunoprecipitate the complex). Methods of measuring protein—protein interaction are well-documented in the art in a variety of publications, including, e.g., Current Protocols in Molecular Biology, (F. M. Ausubel, et al., Eds. 1987, and periodic updates).

In carrying out these methods, DNA-PK complex (i.e., DNA-PKcs and Ku), or an isolated component of a DNA-PK complex, can be used. The Ku polypeptide can be a full-length polypeptide (e.g., has an amino acid sequence of the same length as that found in its natural environment, or "wild-type" sequence), but need not be full-length, as long as the Ku polypeptide retains measurable immunomodulatory nucleic acid molecule binding activity and measurable DNA-PKcs activating activity. The Ku polypeptide used in these assays may also contain alterations in amino acid sequence compared to the wild-type sequence, wherein such alterations may confer a desirable property, including, but not limited to, enhanced stability in vitro, and the like. The Ku polypeptide may further be a fusion protein comprising a Ku polypeptide and a heterologous polypeptide, e.g. a non-Ku polypeptide, including, but not limited to, a epitope to facilitate recovery of the Ku polypeptide from the sample, and the like. Similary, DNA-PKcs used in these assays may be wild-type, or may be a fragment of wild-type; a synthetic fragment; a fusion protein comprising DNA-PKcs or a variant thereof; may comprise one or more amino acid substitutions, additions, insertions, and/or deletions compared to wild-type DNA-PKcs; as long as the DNA-PKcs retains measurable kinase activity toward one or more physiological substrates of wild-type DNA-PKcs and/or retains measurable Ku binding and/or retains measurable binding to other polypeptides that interact with wild-type DNA-PK in vivo or in vitro.

Cell-free assays, i.e., assays which measure a Ku antigen binding to an immunomodulatory nucleic acid molecule, include, but are not limited to, protein-DNA binding assays, electrophoretic mobility shift assays, and the like. Using these methods, one can identify substances that bind specifically to Ku antigen and inhibit binding of a labeled immunomodulatory nucleic acid molecule.

The screening assay can be a binding assay, wherein one or more of the molecules may be joined to a label, and the label directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

Where the method is a cell-free assay method, Ku polypeptide may be, but need not be, substantially purified. In general, the Ku polypeptide should be isolated from the source of Ku in those instances where one or more components found in the source of Ku interfere with binding activity or measurement of binding activity. The sample can be a cell lysate comprising Ku, or the sample can comprise Ku which is purified to any degree. As non-limiting examples, the sample can be: a cell lysate of a mammalian cell line which has been transfected with a recombinant vector ("construct") which encodes and expresses Ku polypeptide having immunomodulatory nucleic acid molecule binding activity; and Ku which has been purified from a biological source.

In some embodiments, the biological activity of DNA-PK being measured is binding of Ku to an immunomodulatory nucleic acid molecule in the test sample. Where the biological activity of Ku being measured is Ku-immunomodulatory nucleic acid molecule binding activity, binding activity may be measured using any known method. In general, the immunomodulatory nucleic acid molecule is labeled with a detectable label, and the amount of label in a complex of Ku and immunomodulatory nucleic acid molecule is an indication of binding activity. Complexes formed upon binding of Ku and immunomodulatory nucleic acid molecule can be detected using antibody specific for Ku, or, if an epitope-tagged Ku antigen is used, an antibody specific for the epitope tag. Immunomodulatory nucleic acid molecules may be labeled with any of a variety of detectable labels, including radioactive labels, biotin, fluorescent labels, and the like. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the nucleic acid molecule is conjugated to biotin, haptens, etc. having a high affinity binding partner, e.g. avidin, specific antibodies, etc., where the binding partner is conjugated to a detectable label.

Agents identified in a cell-free assay may be selected for further study, and assessed for bioavailability, cellular availability, cytotoxicity, biocompatibility, etc.

Where the method is a cell-based assay method, a test sample comprises an intact eukaryotic cell, and an agent to be tested is added. A biological activity of DNA-PK, as described above, can be measured in the intact cell, or in a cell lysate made from the cell. In some embodiments, the test sample further comprises an immunomodulatory nucleic acid molecule.

As a non-limiting example of a cell-based method, a cell which synthesizes DNA-PK is contacted with an immunomodulatory nucleic acid molecule, such that the immunomodulatory nucleic acid molecule enters the cell and binds to Ku. The cell is also contacted with a substance to be tested. The substance to be tested is contacted with the cell either substantially simultaneously with, before, or after, contacting with the immunomodulatory nucleic acid molecule. After a suitable time, Ku binding to the immunomodulatory nucleic acid molecule is assessed, e.g., by lysing the cells, and measuring Ku binding activity in the cell lysates.

Alternatively, the cells need not be lysed in order to measure Ku binding activity. In these embodiments, Ku binding is measured in intact cells. Ku binding may be indicated in intact cells by assaying for secretion of a cytokine, such as IL-6 or IL-12, which is produced by certain cells, such as macrophages, upon Ku-immunomodulatory nucleic acid molecule binding.

As a non-limiting example, a construct comprising a nucleotide sequence encoding Ku polypeptide is introduced into a cell line (e.g., a macrophage cell line, or a cell line that is Ku deficient, e.g., a BMDM cell derived or isolated from a Ku70$^{-/-}$ or Ku 80$^{-/-}$ animal) such that Ku polypeptide is expressed in the cells. For these assays, the Ku coding region may be under control of an endogenous promoter, or, alternatively, under control of an inducible promoter. Inducible promoters are known in the art, and can be used in such a construct. Suitable inducible promoters include, but are not limited to, a hormone-inducible promoter. When an inducible promoter is used, the inducer is added to the cell culture before, or simultaneously with, the substance being tested. Controls include a culture to which no inducer has been added, as well as a culture to which inducer, but no substance being tested, is added. If the assay is conducted in a cell line which is not Ku deficient, a Ku-deficient cell line may be used as a negative control.

Assays such as those described herein are amenable to high through-put screening assays. For example, isolated DNA-PK, isolated Ku, or cells comprising endogenous DNA-PK, or cells expressing a construct encoding DNA-PK complex, or cells expressing a construct encoding Ku, each in separate well of a microtiter plate, e.g., can be contacted with a large number of test compounds at a time, thereby allowing automation.

The term "agent" is used interchangeably herein with the terms "substance" and "compound". An "agent which modulates a biological activity of DNA-PK," as used herein, describes any molecule, e.g. protein; peptide; natural or synthetic inorganic or organic compound, or pharmaceutical, with the capability of altering one or more biological activities of DNA-PK, as described herein. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, and may be natural or synthetic inorganic or organic molecules, which may be small inorganic or organic compounds having a molecular weight of more than 50 and less than about 5000 daltons, or which may be larger compounds (e.g., larger than 5000 daltons), such as macromolecules (e.g., polypeptides, glycopeptides, and the like). Candidate agents include naturally-occurring compounds, synthetic compounds, and semi-synthethic compounds. Candidate agents may comprise functional groups necessary for structural interaction with proteins, particularly hydrogen bonding, and typically include at least an amine, carbonyl, hydroxyl or carboxyl group, or at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, glycosylation, amidification, etc. to produce structural analogs.

A variety of other reagents may be included in the screening assay. These include reagents like salts, neutral proteins, e.g. albumin, detergents, etc., that are used to facilitate optimal nucleic acid-protein binding, and/or protein—protein binding, and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 hour and 1 hour will be sufficient.

Agents Identified by the Screening Methods of the Invention

The invention further provides an agent identified by a screening method of the invention (an "identified agent"), and compositions comprising an identified agent. Compositions may comprise a single agent, or may comprise a mixture of two or more different agents, depending on the desired effect on an immune response or on cell viability. These compositions may comprise a buffer, which is selected according to the desired use of the agent(s), and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Methods Using Identified Agents

The present invention provides methods of modulating an immune response in an individual, generally comprising administering an identified agent to an individual. Agents identified by the screening methods of the invention may enhance, mimic, or inhibit an activity of an immunomodulatory nucleic acid molecule, and may therefore modulate an immune response in an individual. Immunomodulatory nucleic acid molecules may increase a Th1 or a Th2 immune response in a eukaryotic cell. Thus, an identified agent may enhance, mimic, or inhibit a Th1 or a Th2 immune response in a eukaryotic cell. An identified agent can also be used in methods to modulate cell death, and methods of reducing DNA damage, which methods are described above.

In some embodiments, methods are provided for increasing a Th1 response in an individual, comprising administering the agent to an individual. The agent may be administered before, simultaneously with, or after the subject is exposed to antigen. Exposure to antigen can be via intentional introduction by a clinician, other medical personnel, or researcher, or may be via random, unintentional encounter with antigen. Whether a Th1 response is increased, induced, or enhanced can be determined by measuring any parameter associated with a Th1 response, including, but not limited to, production of cytokines normally associated with a Th1 response, including, but not limited to, IL-2 and IFN-γ; and production of Ig2a or its equivalent, an antibody isotype normally associated with a Th1 response. Cytokine production can be measured by any known means, including, but not limited to, a polymerase chain reaction (PCR), using oligonucleotide primers specific for a cytokine; enzyme-linked immunosorbent assay (ELISA), using cytokine-specific antibody; and the like.

In some embodiments, an identified agent may be used in methods for reducing, or inhibiting, a Th2 response in a vertebrate host, comprising administering the agent to an individual. The agent may be administered before, simultaneously with, or after the subject is exposed to antigen. Whether a Th2 response has been reduced or inhibited can be determined by measuring any parameter associated with a Th2 response, using any method known in the art, including, but not limited to, measuring cytokine production normally associated with a Th2 response, including, but not limited to, IL-4, IL-6, and IL-10; and measuring production of antibody isotypes normally associated with a Th2 response, including IgA, and IgE, and IgG1, or their equivalents.

In the above-described methods, the identified agent is generally administered in a formulation together with a pharmaceutically acceptable excipient, as described above. An identified agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the identified agent and/or the desired effect on the immune response. The composition comprising an identified agent can be administered in a single dose or in multiple doses, and may encompass administration of booster doses, to elicit and/or maintain the desired effect on the immune response. Although the dosage used will vary depending on the clinical goals to be achieved, a suitable dosage range is one which provides up to about 1 µg to about 1,000 µg or about 10,000 µg of immunomodulatory nucleic acid molecule can be administered in a single dose. Single or multiple doses can be administered. Appropriate doses and regimens can be readily determined by the clinician.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1
Identification of an ISS-binding Protein

The putative immunostimulatory (ISS) binding protein was isolated by using a multi-step purification strategy. Crude mouse liver lysates were used as the protein source after confirming liver responsiveness to intravenous ISS injection in vivo.

Liver Cells Respond to ISS
Protocols

ISS oligodeoxynucleotide (ISS-ODN) (5'-TGACTGTGAACGTTCGAGATGA-3'; SEQ ID NO: 1) and mutated (M-ODN) (5'-TGACTGTGAACCTTAGAGAA-3'; SEQ ID NO: 2) phosphodiester or phosphorothioate ODNs were purchased from Trilink Biotechnologies (San Diego, Calif.). Total cellular RNA was isolated from spleen of ISS-ODN, M-ODN or PBS injected mice using Stratagene RNA isolation kit (San Diego, Calif.) and subjected to reverse transcription-polymerase chain reaction (RT-PCR). First strand cDNA preparation and PCR amplification were performed using the SuperScript preamplification system (Gibco BRL, Gaithersburg, Md.) and AdvanTaq Plus DNA polymerase (Clontech, San Francisco, Calif.), respectively. The primer sequence used were as follows:

```
IL-6
sense
5'-ATGAAGTTCCTCTCTGCAAGAGACT-3'    (SEQ ID NO:3)

antisense
5'-CACTAGGTTTGCCGAGTAGATCTC-3'     (SEQ ID NO:4)

IL-12p40
sense
5'-GGGACATCATCAAACCAGACC-3'        (SEQ ID NO:5)

antisense
5'-GCCAACCAAGCAGAAGACAGC-3'        (SEQ ID NO:6)

GAPDH
sense
5'-ACCACAGTCCATGCCATCAC-3'         (SEQ ID NO:7)

antisense
5'-TCCACCACCCTGTTGCTGTA-3'         (SEQ ID NO:8)
```

PCR were performed under the following conditions by appropriate cycling number (94° C. for 30 seconds; 65° C. for 30 seconds; and 68° C. for 30 seconds). PCR products were visualized by electrophoresis on 1.5% TAE agarose gels after being stained with ethidium bromide. BMDM isolated from either wild type or Ku 70$^{-/-}$ mice were treated with ISS (10 µg/ml) or LPS (10 µg/ml) or left untreated for 6.5 hours. Total RNA was isolated and 10 µg of total RNA was separated on 1% agarose gel and then transferred onto a nylon membrane. The membrane was probed with [$^{32}$P]-labeled IL-6 or IL-12 or GAPDH cDNA followed by autoradiography, as described previously. Chu et al. (1999) *Immunity* 11:1.

Results

Mice were intravenously injected with 200 µl (1 µg/µl in PBS) of single-stranded (ss) or double-stranded (ds) ISS-ODN (5'-TGACTGTGAACGTTCGAGATGA-3'; SEQ ID NO: 1), ss or ds inactive, mutated (M), M-ODN (5'-TGACTGTGAACCTTAGAGATGA-3'; SEQ ID NO: 9), or 200 µl of 1×PBS. After 2.5 hours, the mice were euthanized and RNA extracted from their livers. This RNA was used in an RT-PCR assay to detect the presence of IL-6, IL-12 and GAPDH messages. The M-ODN did not display any immune stimulation. In contrast, both IL-6 and IL-12 message was readily detected in mice injected with ISS-ODN. The results are shown in FIG. 1A.

Purification of the ISS Binding Protein

Purification of the ISS binding protein was accomplished by sequential ion exchange, heparin and ISS-ODN affinity chromatography, as follows. Due to the relative small tissue weight per spleen, liver lysate was used after confirming its reactivity to in vivo ISS injection, as described above. Crude liver extracts from 220 mice (BALB/c, Jackson Lab., Bar Harbour, Me.) or 15 New Zealand White rabbits (Simunek, Vista, Calif.) were prepared in homogenization buffer (20 mM HEPES, pH 7.6, 250 mM KCl, 0.1 mM EDTA, 0.5 mM EGTA, 20% glycerol) with 250 mM KCl and protease and phosphatase inhibitors and then centrifuged at 100,000×g for 1.5 hours at 4° C. The supernatant (400 ml) was filtered and loaded onto a Porous 20 QE column (17 ml, Pharmacia). Two µl (10 µg) of each fraction were used in a gel retardation assay to identify the location of proteins containing DNA binding activity using [$^{32}$P]-labeled ds-ISS-ODN as a probe. Fractions containing ISS-ODN binding activity were pooled (450 ml), buffered exchanged to low salt (50 mM KCl) and loaded onto a Heparin column (2 ml). The active fractions were subsequently loaded onto a 2 ml ds-ISS-ODN affinity column [CNBr-activated Sepharose 4B (Pharmacia) coupled to 320 μg of ds-ISS-ODNs with the sequence 5'-TGACTG AACGTTCGAGATGA-3'; SEQ ID NO: 21]. The column was washed with 8 ml of homogenization buffer containing 50 mM KCl and the bound proteins were eluted with a 20 ml linear gradient of 50 mM to 1.55 M KCl. One-ml fractions were collected and 2 μl of each were used to test for DNA binding activity. The active fractions were concentrated, separated by SDS-PAGE and stained with Coomassie Blue. The appearance of two bands with estimated molecular weights of 70 KDa and 80 KDa correlated with the DNA binding activity. Sequence analysis (Harvard Microsequencing Facility) of peptides derived from the two bands identified Ku70 and Ku80, respectively.

Mouse liver extracts were purified through anion (QE), heparin and ISS-based affinity chromatography, as described above. Two μl of each fraction (10 μg) were incubated with [$^{32}$P]-labeled ds-ISS-ODN at 4° C. for 30 minutes. The samples were separated on a 5% acrylamide gel and the protein-DNA complexes were detected by autoradiography. Only three fractions from the final affinity column displayed selective reactivity with [$^{32}$P]-labeled ds-ISS-ODN. The active fractions were separated by sodium dodecyl sulfate-polyacrylamide gel electrophoresis (SDS-PAGE), stained with Coomassie blue and micro-sequenced.

Sequence analysis of peptides derived from the two bands identified the Ku70/Ku80 heterodimer as an ISS binding protein. Fractions from the ISS-ODN affinity column were separated by SDS-PAGE and stained with Coomassie blue. Sequence analysis of two bands with approximate molecular sizes of 64 KDa and 97 kDa, which correlated with the presence of DNA binding activity were identified as Ku70 and Ku80, respectively (arrows). The results are shown in FIG. 1B. The Ku heterodimer was identified as an ISS binding protein in four independent experiments.

The Ku heterodimer was further confirmed as an ISS binding protein in a supershift assay using anti-Ku Abs. Ten μg of fraction 20 from the affinity column were incubated with anti-Ku or control (JNK) monoclonal antibodies (mAbs) for 30 minutes prior to probing with ds [$^{32}$P]-labeled ISS-ODN in an electrophoretic mobility shift (EMSA) assay.

To verify the binding specificity of the Ku protein to ISS-ODN, inhibition studies were performed using cold ss or ds ISS or mutated (M, i.e., control) ODNs. The results are shown in FIGS. 1C and 1D. Ten μg of fraction 20 from the affinity column were incubated with [$^{32}$P]-labeled ISS-ODN in the presence of unlabeled (0.1, 0.2 and 0.4 μg, respectively) ss-ISS-ODN (lanes 3–5), ds-ISS-ODN (lanes 7–9), ss-M-ODN (lanes 11–13) or ds-M-ODN (lanes 15–17). As shown in FIGS. 1C and 1D, both cold ds and ss-ISS-ODNs displaced the interaction of [$^{32}$P]-labeled ds-ISS-ODN with Ku from the eluted fraction while the ds and ss-M-ODNs did not have any significant effect on this interaction.

The specific interaction of Ku with ISS-ODN and the lack of interaction of Ku with M-ODN correlates with cytokine induction by ISS-ODN and the lack of induction by M-ODN (FIG. 1A). Following the same methodology, the Ku protein was also isolated and identified as a specific ISS binding protein from crude rabbit liver extract.

Example 2

ISS Stimulate Secretion of IL-6 and IL-12 from Bone Marrow-derived Macrophages from Wild-type Control Mice, but not from Ku70$^{-/-}$ or Ku80$^{-/-}$ Mice.

To evaluate the potential role of Ku in ISS induction of IL-6 and IL-12, bone marrow derived macrophages (BMDM) were grown from wild type (wt), Ku70$^{-/-}$ and Ku80$^{-/-}$ mice and stimulated with ISS-ODN. Martin-Orozco et al. (1999) *Int. Immunol.* 11:1111.

Ku70$^{-/-}$ and Ku80$^{-/-}$ mice and their wild-type (wt) control on the 129 genetic background were generated by Dr. G. Li and bred at Memorial Sloan-Kettering Cancer Center (MSKCC), New York, N.Y. BMDM from wt, Ku70$^{-/-}$ and Ku80$^{-/-}$ mice (MSKCC) were prepared as was previously published (Martin-Orozco et al. (1999) *Int. Immunol.* 11:1111), and maintained in DMEM with 10% FBS, antibiotics and 20% L-cell medium and cultured for about 10 days to allow them to mature. BMDM were seeded (2.5× 10$^5$/well in triplicate) on 96-well plates and treated with LPS (10 μg/ml), ISS-ODN (5 μg/ml) or M-ODN (5 μg/ml).

Figure 2B:
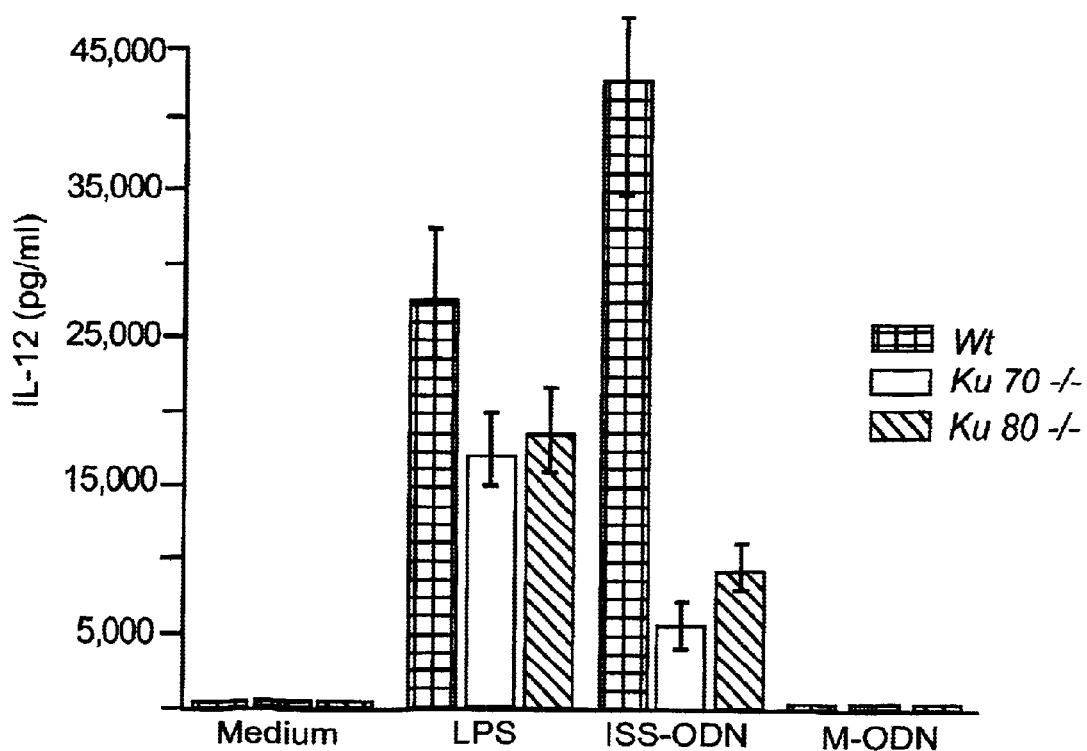

The results are shown in FIGS. 2A–C. BMDM (2.5×10$^5$/ well) from wt, or Ku70$^{-/-}$ and Ku80$^{-/-}$ mice were treated with LPS (1 μg/ml), ISS-ODN (5 μg/ml) or M-ODN (5 μg/ml) for 24 hours. IL-6 (A) or IL-12 (B) levels in the supernatants were determined by ELISA. Results are means±S.D. of 5 separate experiments for wt and Ku70$^{-/-}$ and 3 separate experiments for Ku80$^{-/-}$ mice. (C) BMDM were incubated with LPS (10 μg/ml) or ISS-ODN (5 μg/ml) for 6.5 hours. Total RNA was isolated and analyzed for the presence of IL-6, IL-12 and GAPDH messages by a Northern blot assay, as described in Example 1. Results are means±S.D. of 5 separate experiments for wt and Ku70$^{-/-}$ and 3 separate experiments for Ku80$^{-/-}$ mice.

As shown in FIGS. 2A–C, BMDM from Ku70$^{-/-}$ and Ku80$^{-/-}$ mice secreted very low levels of IL-6 (FIG. 2A) and IL-12 (FIG. 2B) as compared to BMDM from wt controls. The diminished response was ISS specific since LPS stimulation resulted in the induction of IL-6 and IL-12 from both wt and Ku70$^{-/-}$ BMDM. The lack of induction of IL-6 and IL-12 by ISS in Ku70$^{-/-}$ or Ku80$^{-/-}$ BMDM was further confirmed by Northern blot analysis (FIG. 2C). These data further confirm that ISS binds Ku antigen to mediate its effects.

Example 3

DNA-PKcs is Required for Innate Cytokine Induction by Bacterial DNA and ISS-ODN

Materials and Methods

DNA-PKcs$^{-/-}$ and their wt control mice on the 129 genetic background were generated by Dr. G. C. Li and bred at Memorial Sloan-Kettering Cancer Center, New York, N.Y. IKKβ$^{-/-}$ Tnfr1$^{-/-}$ mice were generated by Drs. Z-W Li and Karin M. ATM$^{-/-}$ mice on the C57BL/6 background were generated and bred by Dr. Y. Xu (UCSD) as was previously described (Xu et al.(1996) *Genes Dev.* 10:2411–2422) while their wild-type (wt) control were purchased from Jackson Laboratories (Bar Harbor, Me.). BMDMs from wt, DNA-PKcs$^{-/-}$ mice, IKKβ$^{-/-}$ Tnfr1$^{-/-}$ and ATM$^{-/-}$ mice were prepared as was previously published (Martin-Orozco et al. (1999) *Intl. Immunol.* 11:1111–1118), maintained in DMEM with 10% FBS, antibiotics and 20% L-cell medium and cultured for 7–10 days to allow them to mature. Prior to use BMDM were seeded (2.5×10$^5$/well in triplicate) in 96-well plates and than treated with LPS (1 μg/ml), ISS-ODN (5 μg/ml) or M-ODN (5 μg/ml), po-ISS-ODN (10 μg/ml) or po-ds-ISS-ODN (10 μg/ml), LPS-free, ultra pure bacterial DNA (*E. coli*, Sigma) (15 μg/ml) or methylated bacterial DNA or LPS-free, ultra pure calf thymus DNA (Sigma) (15 μg/ml). Methylation of bacterial DNA was performed by SssI methylase (Biolab, Boston, Mass.) (15 μg/ml) following manufacturer's instruction. Where indicated the PI3K inhibitor wortmannin (Wm), at various concentrations, was added to ISS-ODN or LPS stimulated BMDMs. After 24 hours in culture, the supernatants were collected and assayed for IL-6 and IL-12 levels by ELISA kits (PharMingen, San Diego, Calif.).

Most of the experiments described in this study were performed with LPS-free, single stranded (ss), 22 mer long, phosphothioate (ps) ODNs. In some experiments, ss and double stranded (ds) 22 mer long phosphodiester (po) ODNs were used. (Trilink, San Diego, Calif.). The sequences of the ODNs used in this study are as follows (where *C denotes 5-methyl C):

| | | | |
|---|---|---|---|
| ISS-ODN (1) | 5'-TGACTGTGAACGTTCGAGATGA-3' | (SEQ ID NO:1) |
| ISS-ODN (2) | 5'-TGACTGTGAACGTTAGAGATGA-3' | (SEQ ID NO:10) |
| Methylated ($^{5\text{-methyl}}$C) ISS-ODN | 5'-TGACTGTGAA*CGTTAGAGATGA-3' | (SEQ ID NO:11) |
| Mutated (M)-ODN | 5'-TGACTGTGAAGGTTAGAGATGA-3' | (SEQ ID NO:12) |
| Control-ODN (1) | 5'-TGACTGTGAACCTTAGAGATGA-3' | (SEQ ID NO:9) |
| Control-ODN (2) | 5'-TGACTGTGTTCCTTAGAGATGA-3' | (SEQ ID NO:13) |
| Control-ODN (3) | 5'-TGACTGTGAATATTAGAGATGA-3' | (SEQ ID NO:14) |

Results

Figure 3A:
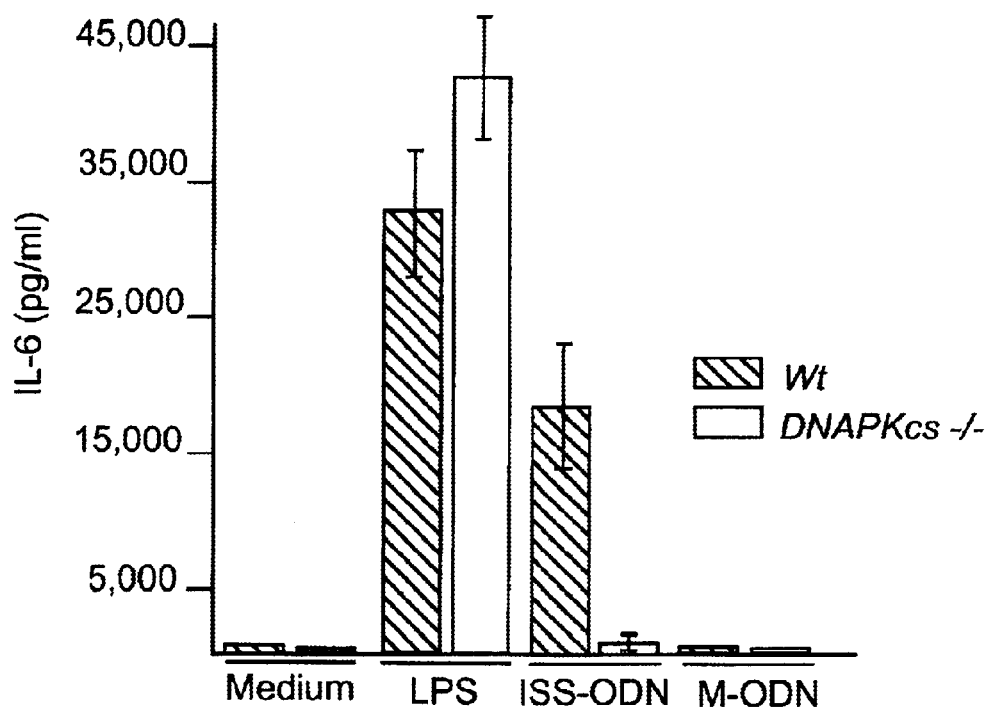
Figure 3B:
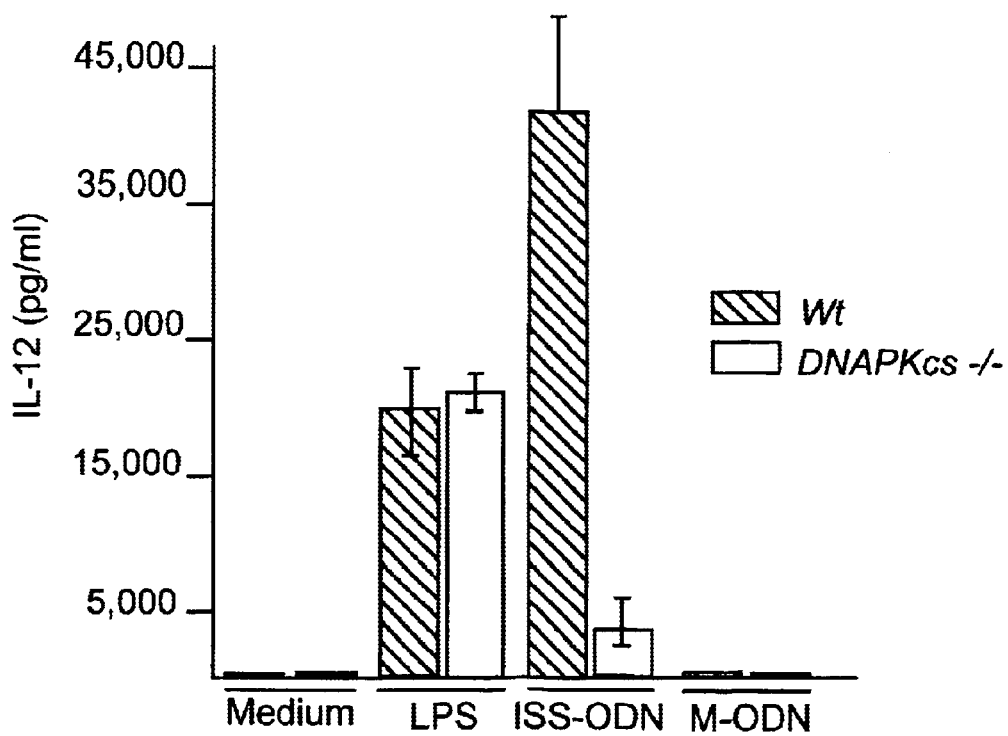

Bone marrow-derived macrophages (BMDM) respond to ISS-ODN by secreting high levels of IL-6 and IL-12. Martin-Orozco et al. (1999) *Int'l. Immunol.* 11:1111–1118. Initially, BMDM from DNA-PKcs-deficient mice (Kurimasa et al., 1999) were used to explore the possible role of DNA-PKcs in induction of these innate cytokines by ISS-ODN. Very low levels of IL-6 and IL-12 were produced by DNA-PKcs-deficient BMDM upon ISS-ODN stimulation in comparison to wild type (wt) BMDM, as shown in FIGS. 3A and 3B. In contrast, DNA-PKcs$^{-/-}$ BMDM exhibited normal induction of IL-6 and IL-12 in response to LPS stimulation, as shown in FIGS. 3A and 3B.

Since phosphothioate (ps) ODNs differ structurally from phosphodiester (po) ODNs, we compared the response of ISS-ODN to po-ISS-ODN, po-ds-ISS-ODN (unmethylated or methylated), LPS-free bacterial DNA (*E. coli*,), methylated *E. coli* bacterial DNA or to LPS-free calf thymus DNA. Similar activity profile was observed for po-ds-ISS-ODN and bacterial DNA in wt BMDM (FIGS. 3C and 3D) while po-ISS-ODN was less effective FIGS. 3C and 3D). As expected, calf thymus DNA and methylated bacterial DNA induced a several-fold less IL-6 and IL-12 as compared to unmethylated bacterial DNA. BMDM from DNA-PKcs-deficient mice were also defective in induction of IL-6 and IL-12 in response to po-ISS-ODN, po-ds-ISS-ODN and bacterial DNA (FIGS. 3C and 3D), indicating that DNA-PKcs is required for induction of IL-6 and IL-12 by synthetic (ps) and natural forms (po) of ISS-enriched DNAs (i.e., bacterial DNA).

Figure 3C:
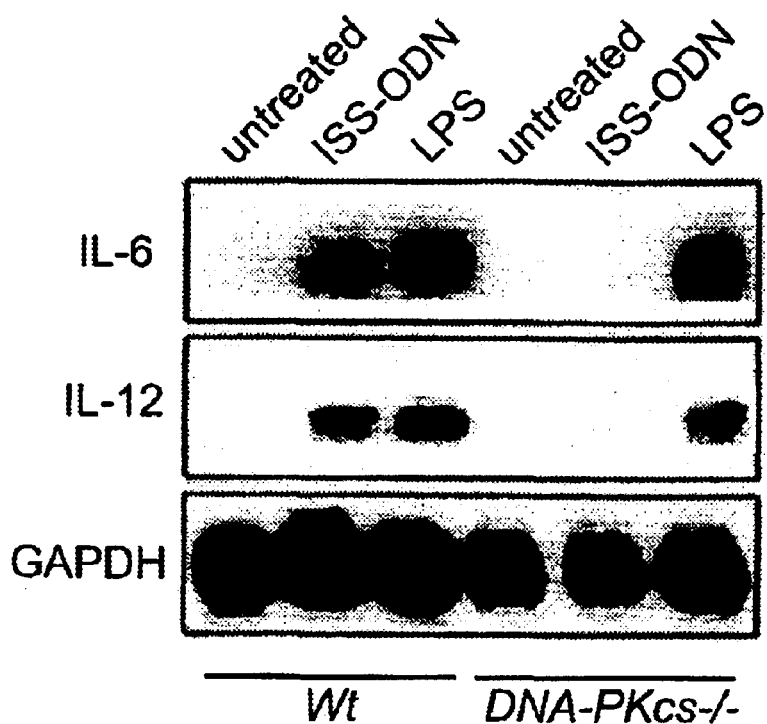

We then determined whether the lack of ISS-ODN responsiveness in DNA-PKcs-deficient BMDM was due to a defect in mRNA induction. Little induction of IL-6 and IL-12 mRNAs in response to ISS-ODN was observed in DNA-PKcs-deficient BMDM (FIG. 3C). In contrast, DNA-PKcs-deficient BMDM exhibited normal cytokine mRNA induction in response to LPS stimulation.

Figure 3D:
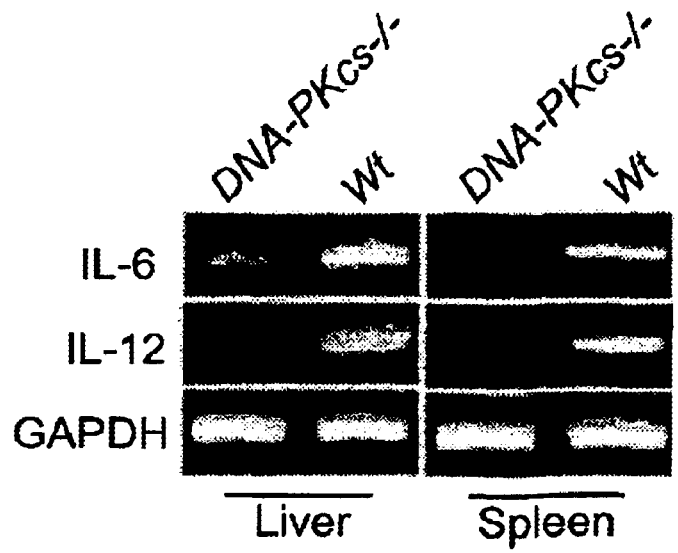

To determine the requirement for DNA-PKcs in the induction of IL-6 and IL-12 by ISS-ODN, po-ISS-ODN, ps-ds-ISS-ODN, bacterial and calf thymus DNAs in vivo, we injected these DNAs to wt and DNA-PKcs$^{-/-}$ mice. The levels of IL-6 and IL-12 mRNAs in liver or spleen were examined by RT-PCR. IL-6 or IL-12 mRNA levels were detected in the liver or the spleen of wt controls but were lacking in the same organs in DNA-PKcs-deficient mice (FIG. 3D). Only minute amounts of mRNAs were observed in response to calf thymus DNA injection into wt mice (FIG. 3D).

Figures 4E, 4F:
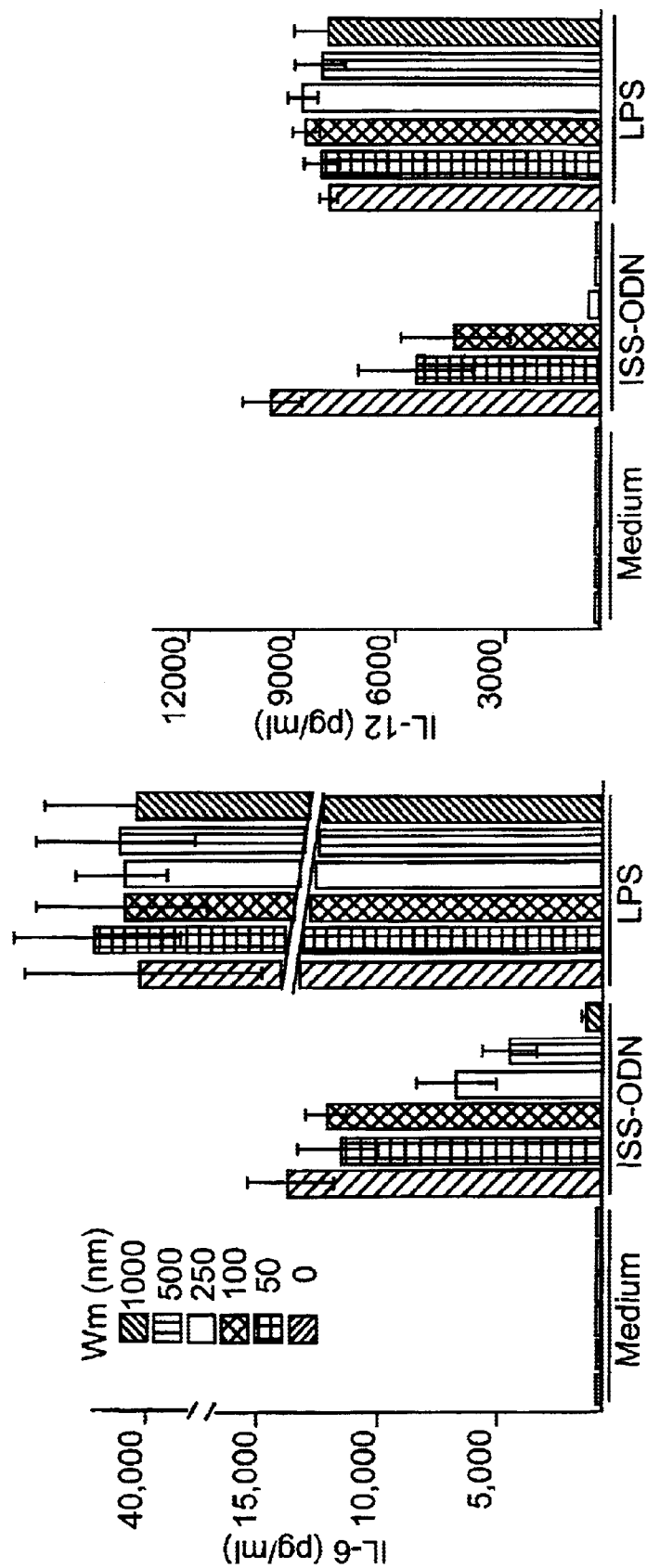

DNA-PKcs is a member of PI3K family and its enzymatic activity is blocked by PI3K inhibitors such as wortmannin (Wm) at high concentrations, or Ly294002 (Ly). Hartley et al.(1995) *Cell* 82:849–856; and Smith and Jackson (1999) *Genes Dev.* 13:916–934. To further establish the role of DNA-PKcs in the induction of IL-6 and IL-12 by ISS-ODN, we examined the effects of Wm and Ly on these responses. High concentrations of Wm (>100 nM) significantly inhibited the induction of IL-6 and IL-12 by ISS-ODN (Hartley et al., 1995) (FIGS. 4E and 4F). Ly also blocked IL-6 and IL-12 induction by ISS-ODN. In contrast, both Wm and Ly did not inhibit LPS-induced secretion of IL-6 and IL-12 FIGS. 4E and 4F).

The ATM gene product, which is also a member of the PI3K family, is functionally related to DNA-PKcs and its kinase activity is also Wm and Ly sensitive (Hartley et al., supra; Xu et al., supra). We therefore examined the induction of IL-6 and IL-12 in ATM-deficient mice. As shown in FIGS. 4G and 4H, normal induction of IL-6 and IL-12 by ISS-ODN was observed in ATM-deficient BMDM, excluding a role for ATM in ISS-induced activation of innate immunity.

Example 4

IKKβ is Essential for ISS Activity

Materials and Methods

Oligonucleotides

Oligonucleotides were as described in Example 3, above.

Animals

Animal were as described in Example 3, above.

Kinase assays and Immunoblotting.

Kinase assays and immunoblotting were performed according to Li et al. ((1999) *J. Exp. Med.* 189:1839–1845). Briefly, BMDM were treated with ISS-ODN (5 µg/ml), M-ODN (5 µg/ml) on ps and po backbones as indicated, LPS-free bacterial DNA or methylated bacterial DNA (5 µg/ml), LPS-free calf thymus DNA (5 µg/ml), LPS (10 µg/ml) or TNFα (10 ng/ml) for the indicated time periods. Cell lysates were prepared and normalized by immunoblotting (IB) with anti-IKKα polyclonal antibodies (Santa Cruz, Santa Cruz Biotech Inc., Calif.), anti-IKKβ polyclonal antbodies (Santa Cruz) or anti-DNA-PKcs monoclonal antibodies (NeoMarker, Calif.). IκB kinase (IKK) complex or DNA-PK complex from 100 µg of the lysates were immunoprecipitated by anti-IKKα or by anti-DNA-PKcs antibodies. The kinase activities (KA) were determined by a kinase assay using the N-terminus of IκBα (for IKK) or the N-terminus of p53 (for DNA-PK) as a substrate as previously described. Wang et al. (1992) *Proc. Natl. Acad. Sci. USA* 89:4231–4235; Li et al.(1999), supra; and Hammarsten et al. (2000) *J. Biol. Chem.* 275:1541–1545.

The in vitro DNA-PK phosphorylation assay was performed according to Hammarsten et al. (2000), supra, with modification. Briefly, affinity-purified DNA-PK (Promega, Mo.) was incubated with various DNA preparations (described below), 0.5 μg of GST-p53 (1–70) and 3.3 μCi of γ-$^{32}$p-ATP in a 20 μl reaction buffer (10 mM Tris-Cl, 5 mM MgCl$_2$, 0.3 mM EDTA and 10 μM ATP) at 30° C. for 30 minutes. The reaction was stopped by addition of 4× loading buffer. The samples were boiled, loaded on 9% SDS-PAGE, transferred onto a PVDF membrane and visualized by autoradiography.

The ODNs (ps-ss) used include an ISS-ODN with an active CpG motif (AACGTT), a methylated ISS-ODN at the $^5$C of the CpG dinucleotide (AA*CGTT) and various control ODNs. These ODNs were incubated at concentrations of 0, 0.1, 0.3, or 1 ng/reaction. The po-ISS-ODN was incubated at concentration of 20, 50 or 100 ng/reaction. The po-ds-ISS-ODN was incubated at concentration of 0, 0.5, 1, 2, 5 or 10 ng/reaction. The bacterial or calf thymus DNAs were each incubated at concentration of 1, 2 or 5 ng/reaction. Electrophoretic gel mobility shift assay (EMSA) was performed as previously described. Chu et al. (1999) *Immunity* 11:721–731; and Li et al., 1999, supra). In vitro IKK kinase assays were performed using purified IKK derived from Sf9 insect cell lysates as was previously described. Zandi et al. (1998) *Science* 281:1360–1363.

RT-PCR and Northern Blots

Total cellular RNA was isolated from spleen or liver of wt or DNA-PKcs$^{-/-}$ mice injected with ISS-ODN (50 μg), po-ISS-ODN (100 μg), po-ds-ISS-ODN (100 μg), bacterial DNA (100 μg) or calf thymus DNA (100 μg), using a RNA isolation kit (Stratagene, San Diego, Calif.) and subjected to reverse transcription-polymerase chain reaction (RT-PCR). First strand cDNA preparation and PCR amplification were performed using the SuperScript preamplification system (Gibco BRL, Gaithersburg, Md.) and AdvanTaq Plus DNA polymerase (Clontech, San Francisco, Calif.), respectively. The primer sequences used were as follows:

```
IL-6
sense
5'-ATGAAGTTCCTCTCTGCAAGAGACT-3'     (SEQ ID NO:3)
antisense
5'-CACTAGGTTTGCCGAGTAGATCTC-3'      (SEQ ID NO:4)

IL-12p40
sense
5'-GGGACATCATCAAACCAGACC-3'         (SEQ ID NO:5)
antisense
5'-GCCAACCAAGCAGAAGACAGC-3'         (SEQ ID NO:6)

GAPDH
sense
5'-ACCACAGTCCATGCCATCAC-3'          (SEQ ID NO:7)
antisense
5'-TCCACCACCCTGTTGCTGTA-3'          (SEQ ID NO:8)
```

PCR reactions were performed under the following conditions by appropriate cycling number (94° C.: 30 sec, 65° C.:30 sec, 68° C.:30 sec). PCR products were visualized by electrophoresis on 1.5% TAE agarose gels after being stained with ethidium bromide. BMDM isolated from either wild type or DNA-PKcs-deficient mice were treated with ISS-ODN (10 μg/ml), LPS (10 μg/ml) or left untreated for 6.5 hrs. Total RNA was isolated and 10 μg of total RNA was separated on 1% agarose gel and then transferred onto a nylon membrane. The membrane was probed with α-$_{32}$P-dCTP-labeled IL-6 or IL-12 or GAPDH cDNA (generated by RT-PCR as described above) followed by autoradiography.

Methylation and Labeling of Free Ends of Genomic DNAs

When indicated, 100 μg of ultra pure bacterial DNA (*E. coli*, Sigma) was incubated with or without 200 units SssI methylase (Biolab) in a 200 μl reaction buffer according to manufacture instruction at 37° C. for 3 hours and then extracted with phenol/chloroform. The bacterial DNA was precipitated with ethanol and dissolved in TE buffer. One μg of mock and methylated bacterial DNA was further incubated with 10 unit of BstU1 at 60° C. for 4 hrs, loaded on 1% agarose gel and visualized by ethidium bromide (EB) staining for the absence or presence of digest products in the methylated and in the non-methylated bacterial DNA, respectively.

For the DNA-PK assay we measure the free ends in *E.coli* and calf thymus DNAs by labeling the 5' free ends of both the DNA preparations. Thus, 0.2 μg of either bacterial or calf thymus DNAs were incubated with 15 units of T4 PNK (Stratagene, San Diego, Calif.) and 100 μCi of γ-$^{32}$p-ATP in a 20 μl of reaction at 37° C. for 3 hrs. To purify the labeled DNAs from the γ-$^{32}$p-ATP excess, the samples were loaded onto SephdexG50 column (Stratagene San Diego, Calif.) after the reaction was stopped. One μl of labeled DNA was used to measure radioactivity which yielded $4.1 \times 10^6 \pm 2 \times 10^4$ cpm/1 μg for bacterial DNA and $4.2 \times 10^6 \pm 5.2 \times 10^4$ cpm/1 μg for calf thymus DNA.

Results

Figure 5A:
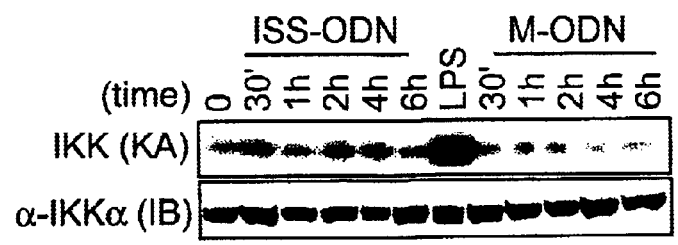
Figure 5B:
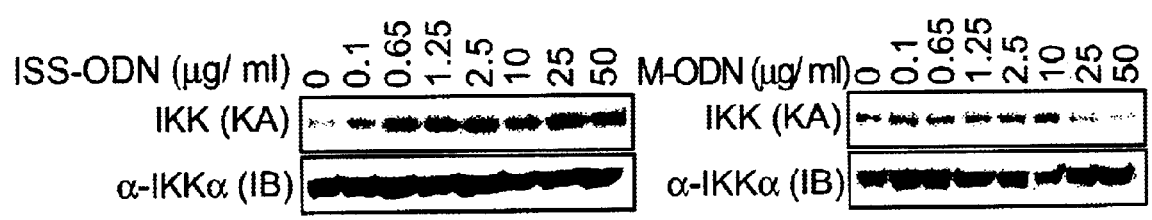

We evaluated whether ISS-ODN activated IKK, which is essential for NF-κB activation by pro-inflammatory stimuli. Karin and Delhase (2000) *Seminars in Immunol.* 12:85–89. We observed maximal IKK activation 30 minutes post-ISS-ODN incubation, which lasted for about 4 hrs in wt BMDM (FIG. 5A). While bacterial DNA and po-ISS-ODN induced IKK activation similar to ISS-ODN, little increase in IKK activity was observed with M-ODN and or calf thymus DNA (FIG. 5A). Optimal IKK activation was observed at an ISS-ODN concentration of 0.65 μg/ml, with little IKK activation in response M-ODN (FIG. 5B).

Figure 5C:
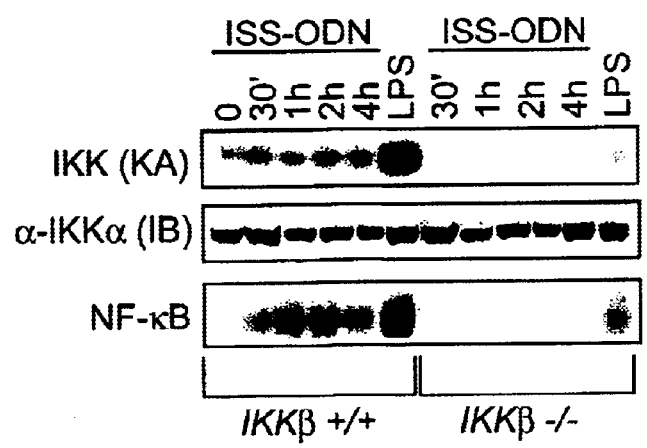

We used BMDM isolated from IKKβ$^{-/-}$ Tnfr$^{-/-}$ mice to determine the requirement of IKK activity, which is highly reduced in these animals. The absence of IKKβ prevented IKK and NF-κB activation by ISS-ODN as well as LPS (FIG. 5C) and significantly reduced the induction of IL-6 and IL-12 (FIGS. 5D and 5E).

Figure 6A:
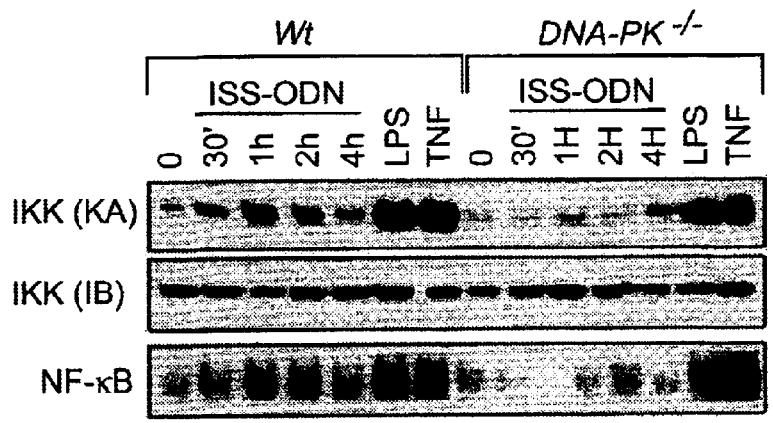
Figure 6B:
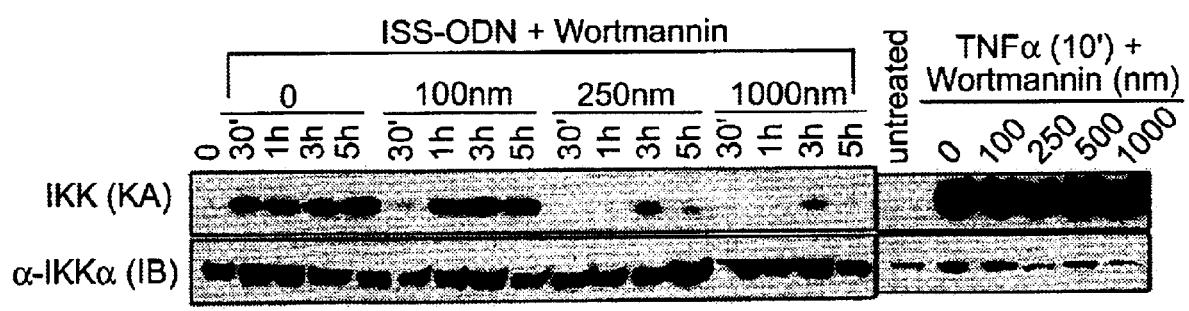

We then examined the dependence of IKK activation by ISS-ODN on DNA-PKcs. While incubation of wt BMDM with ISS-ODN resulted in robust IKK activation, little increase in IKK activity was observed in similarly treated DNA-PKcs$^{-/-}$ BMDM (FIG. 6A). As a result, DNA-PKcs$^{-/-}$ BMDM also exhibited impaired NF-κB activation upon treatment with ISS-ODN (FIG. 6A). By contrast, DNA-PKcs-deficient BMDM were fully responsive to LPS or TNFα. Furthermore, we examined the dependence of IKK activation by bacterial DNA and po-ISS-ODN on DNA-PKcs. As expected, activation of IKK by bacterial DNA or po-ISS-ODN was largely reduced in DNA-PKcs$^{-/-}$ BMDM as compared to their wt controls (FIG. 6B).

Figure 6C:
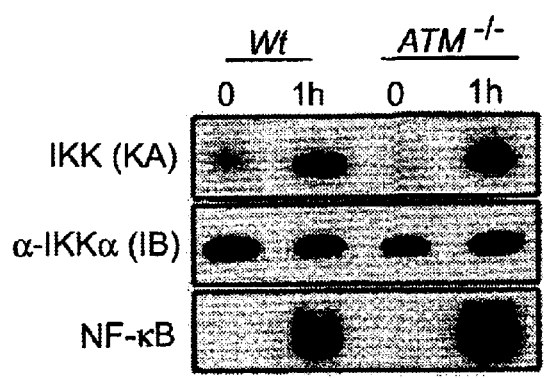

To determine whether DNA-PKcs activity is required for IKK activation we used the PI3K inhibitor Wm. As found for IL-6 and IL-12 production, only high concentrations of Wm (250 nM and above) significantly inhibited IKK activation in wt BMDM by ISS-ODN (FIG. 6C). Even at 1000 nM Wm had no effect on IKK activation by TNFα, while at lower concentrations (50–100 nM) Wm significantly inhibited IKK activation by PGDF. We also compared ISS-ODN-induced of IKK and NF-κB activation in BMDM from wt or ATM-deficient mice (Xu et al., 1996, supra). As shown in FIG. 6D, no differences were observed for ISS-ODNinduced IKK or NF-κB activation between wt and ATM-deficient BMDM, excluding a role of ATM in this signaling.

Taken together, these results indicate that DNA-PKcs acts upstream to IKK and is specifically required for IKK activation by synthetic (ps) and natural forms (po) of ISS-enriched DNAs.

Example 5
ISS-ODN Directly Activates DNA-PK

Materials and Methods

Oligonucleotides and DNA-PK assays were as described in Examples 3 and 4, above.

Results

We investigated whether ISS-ODN can directly activate DNA-PK in vitro. The ability of an ISS-ODN containing the active CpG motif (5'-pur-pur-CpG-pyr-pyr-3' i.e., 5'-AACGTT-3') to specifically stimulate phosphorylation of the N-terminal portion of p53 was compared to a battery of mutated ODNs, which include: 1) a methylated C in the CpG dinucleotide, 2) a CpC basepair instead of the CpG dinucleotide core, 3) a GpG basepair instead of the CpG dinucleotide core, 4) an ApT basepair instead of the CpG dinucleotide core, and 5) a TTCC instead of the AACG sequence of the CpG motif (see Example 4, above). None of the mutant ODNs induced significant secretion of IL-6 or IL-12 upon stimulation of BMDM in vitro. Only the ISS-ODN stimulated DNA-PK activity (FIG. 7A) whereas none of the mutant ODNs, which devoid of biological activity, led to substantial increase in DNA-PK activity.

Figure 7A:
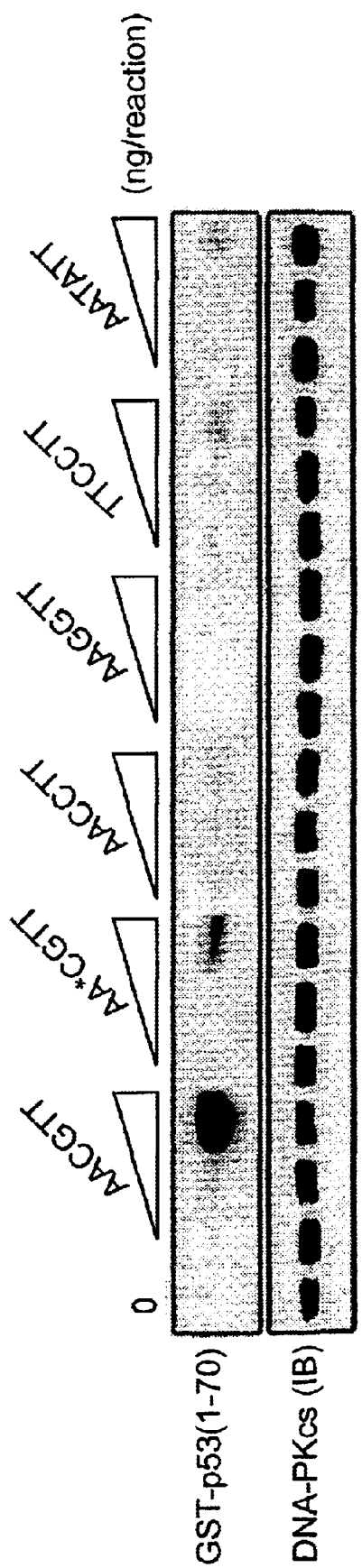
Figure 7B:
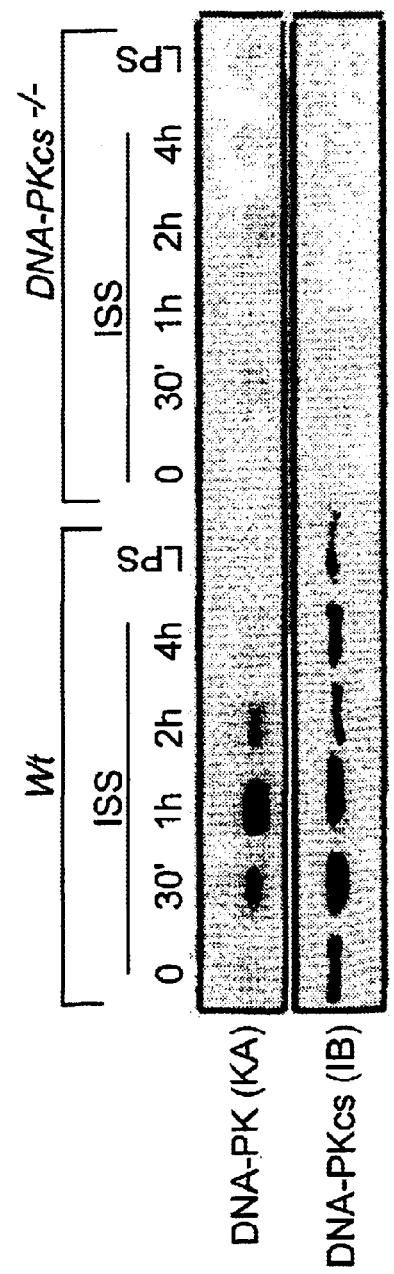

Next, we investigated the ability of po-ISS-ODN to activate DNA-PK in vitro. Unlike ISS-ODN (FIG. 6A), po-ISS-ODNs weakly activated DNA-PK only at higher concentrations (50–100 ng/reaction) (FIG. 7B). By contrast, po-ds-ISS-ODN was almost as potent as ISS-ODN in activating this enzyme (FIG. 7C). Methylated ISS-ODN (AA*CGTT) and methylated po-ISS-ODN (AA*CGTT) were weaker DNA-PK activators than their unmethylated counterparts (FIGS. 7A and 7B, respectively).

In addition, we evaluated the ability of bacterial DNA, methylated bacterial DNA and calf thymus DNA to activate DNA-PK. To use the same equimolar amount of the various DNA preparations in the DNA-PK assays, we first measured the 5' free ends using T4 DNA polynucleotide kinase in the DNA preparations. For bacterial DNA, this labeling yielded $6.29 \times 10^5$ cpm/0.1 μg and $4.1 \times 10^6$ cpm/1 μg of DNA and for calf thymus DNA it yielded $8.58 \times 10^5$ cpm/0.1 μg and $4.2 \times 10^6$ cpm/1 μg of DNA. Under these conditions, calf thymus DNA was a weaker activator of DNA-PK than bacterial DNA (FIG. 7D) while methylated bacterial DNA was a less potent DNA-PK activator than unmethylated bacterial DNA (FIG. 7E).

To further determine whether ISS-ODN, po-ISS-ODN or bacterial DNA activate DNA-PK in cells, we treated BMDM from either wt or DNA-PKcs-deficient mice with ISS-ODN, po-ISS-ODN, bacterial DNA or LPS as a control. Considerable DNA-PK activity, as measured by immune-complex kinase assay, was found after a 30-minute incubation with ISS-ODN, po-ISS-ODN or bacterial DNA which peaked after 1 hour (FIG. 7F). Little or no DNA-PK activity was detected in DNA-PKcs-deficient BMDM and LPS had no effect on DNA-PK activity even in wt cells.

Example 6
DNA-PK Phosphorylates IKKβ

Materials and Methods

Oligonucleotides and assays were as described in Examples 3 and 4, above.

Results

Figure 8A:
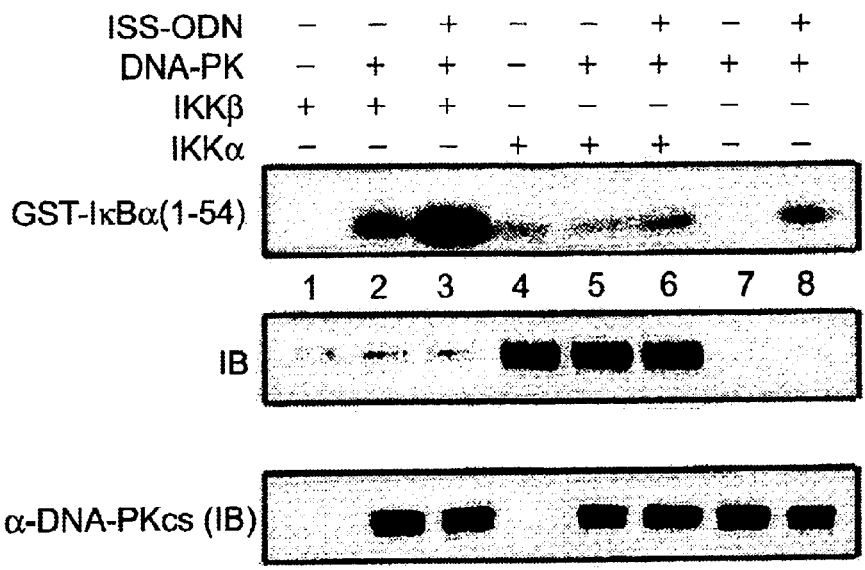
FIGS. 8A and 8B depict results showing that DNA-PK activates IKKβ through phosphorylation.
Figure 8B:
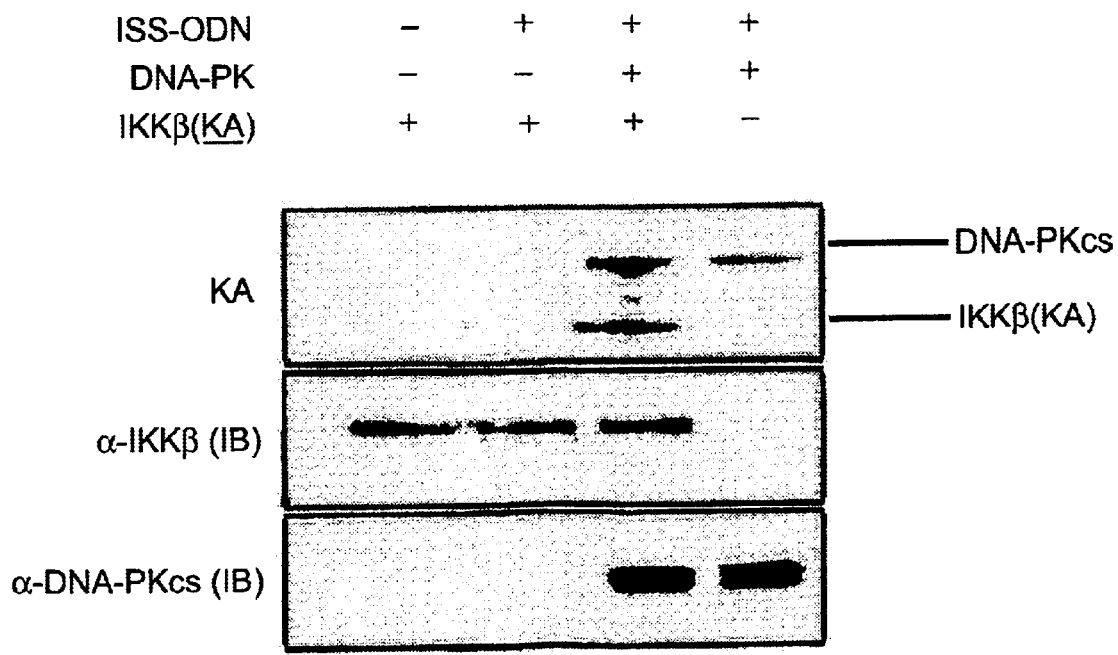
Figure 9:
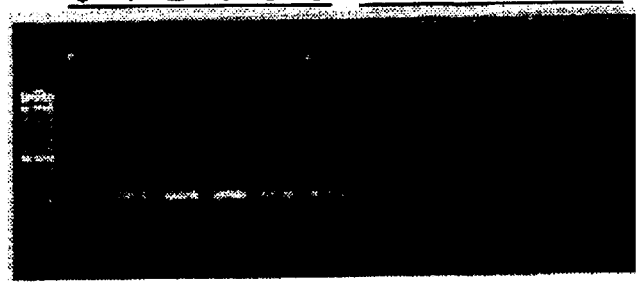
FIG. 9 depicts result showing induction of HSP70 by ISS.
Figure 9:
Figure 9:
Figure 9:
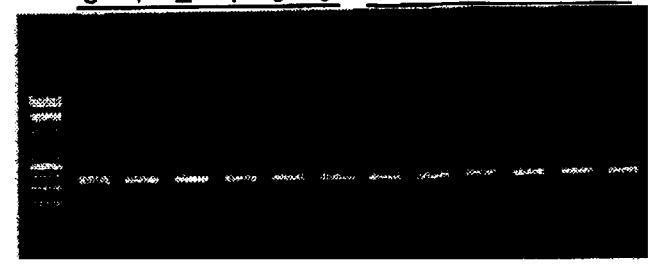
Figure 10:
FIG. 10 depicts results showing that induction of inducible HSP70 by ISS is IFNα/β-dependent.
Figure 10:
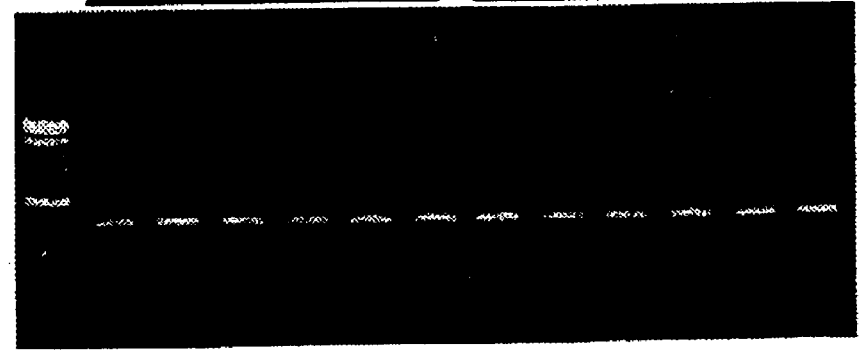

To explore a role of ISS-activated DNA-PK in IKK activation we tested whether affinity-purified DNA-PK can directly activate recombinant IKKα or IKKβ purified from Sf9 cells (Zandi et al., 1998, supra). Recombinant IKKα and IKKβ display considerable basal kinase activity (Zandi et al., 1998, supra; Chu et al., 1999, supra) but incubation of IKKβ with DNA-PK in the presence of ISS-ODN further increased its kinase activity measured by IκB phosphorylation (FIG. 8A). Furthermore, although DNA-PKcs phosphorylated IκBα that activity was considerably lower than that achieved by IKKβ plus DNA-PK. Only a small enhancement of IκB kinase activity was found upon incubation of IKKα with DNA-PK in the presence of ISS-ODN, but not beyond the level found with DNA-PK alone (FIG. 8A, lane 6 vs. 5). To further confirm the activation of IKKβ by DNA-PK, we performed a coupled-kinase assay. Recombinant IKKβ was pre-incubated with DNA-PK in the presence or absence of ISS-ODN followed by immunoprecipitation of IKKβ and IκB kinase activity was measured. Consistent with the results described above, DNA-PK only activates IKKβ in the presence of ISS-ODN. We next determined whether DNA-PK phosphorylates IKKβ. Recombinant catalytically inactive IKKβ [IKKβ (KA)] purified from Sf9 cells was incubated with or without DNA-PK, in the presence or absence of ISS-ODN. As shown in FIG. 8B, DNA-PK phosphorylated IKKβ (KA) when incubated with ISS-ODN.

Example 7
ISS Induces HSP70 Gene Transcription

A half million mouse BMDM isolated from BALB/c, IFNα receptor knockout, or IFNγ knockout mice were incubated with ISS-ODN or M-ODN at a final concentration of 10 μg/ml. After 0, 1, 2, 4, 6, and 8 hours, total RNA was prepared and analyzed by RT-PCR (reverse transcription-polymerase chain reaction) for induction of gene transcription of heat shock proteins. The sequences of the primers used is as follows:

```
hsp70
(forward)
5'GAG ATC ATC GCC AAC GAC CA 3'      (SEQ ID NO:15)

hsp70
(reverse)
5'ACA GTC TTT CCG AGG TAT CG 3'      (SEQ ID NO:16)

hsc70
(forward)
5'AAT GAC GAG GGT AAC GGG AG 3'      (SEQ ID NO:17)

hsc70
(reverse)
5'ACA GTG TTT GGG AGG TAT GG 3'      (SEQ ID NO:18)

hsp90
(forward)
5'ATG AGG GTG CTG TGG GTG TT 3'      (SEQ ID NO:19)

hsp90
(reverse)
5'GAG TTC AGG TTG GAA GGG GA 3'      (SEQ ID NO:20)

G3PDH
(forward)
5'ACG ACA GTG CAT GCG ATC AC 3'      (SEQ ID NO:7)

G3PDH
(reverse)
5'TCC AGC ACG GTG TTG GTG TA 3'      (SEQ ID NO:8)
```

The results are shown in FIGS. 9A–D and FIGS. 10A and B. The data presented in these figures provide evidence that ISS induces inducible HSP-70. This induction is dependent on type 1 IFN, because stimulation of BMDM from IFN type 1 receptor knockout mice did not result in induction of HSP-70.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for identifying an agent that modulates a biological activity of DNA-PK, comprising:
   a) adding an agent to be tested to a sample, the sample comprising DNA-PK and an immunomodulatory nucleic acid molecule, under conditions which favor binding of the immunomodulatory nucleic acid molecule to DNA-PK, thereby forming a test sample, wherein the immunomodulatory nucleic acid molecule is a DNA molecule that, when bound to Ku antigen, activates DNA-PKcs, wherein the immunomodulatory nucleic acid molecule comprises a nucleotide sequence selected from 5'-Purine-Purine-C-G-Pyrimidine-Pyrimidine-3',5'-Purine-TCG-Pyrimidine-Pyrimidine-3',5'-(TCG)$_n$-3', where n is an integer that is 1 or greater, 5'-Purine-TCG-Pyrimidine-Pyrimidine-CG-3', and 5'-Purine-Purine-CG-Pyrimidine-Pyrimidine-CG-3'; and
   b) detecting a biological activity of DNA-PK protein in the test sample, as compared to a control sample lacking the agent, wherein an increase or a decrease in the biological activity of DNA-PK indicates that the agent modulates a biological activity of DNA-PK.

2. The method of claim 1, wherein the biological activity of DNA-PK is binding to an immunomodulatory nucleic acid molecule.

3. The method according to claim 2, wherein the method is a cell-free method, and the immunomodulatory nucleic acid molecule is detectably labeled.

4. The method of claim 1, wherein the biological activity of DNA-PK is activation of DNA-PKcs kinase activity.

5. The method of claim 1, wherein the method is a cell-based method and modulation of DNA-PK activity is detected by measuring an amount of IL-6 or IL-12 produced by the cell.

6. A method for identifying an agent that modulates a biological activity of DNA-PK, comprising:
   a) adding an agent to be tested to a sample, the sample comprising DNA-PK and an immunomodulatory nucleic acid molecule, under conditions which favor binding of the immunomodulatory nucleic acid molecule to DNA-PK, thereby forming a test sample, wherein the immunomodulatory nucleic acid molecule is a DNA molecule that, when bound to Ku antigen, activates DNA-PKcs, wherein the immunomodulatory nucleic acid molecule comprises a nucleotide sequence selected from 5'-Purine-Purine-C-G-Pyrimidine-Pyrimidine-3',5'-Purine-TCG-Pyrimidine-Pyrimidine-3';5'-(TCG)$_n$-3', where n is an integer that is 1 or greater, 5'-Purine-TCG-Pyrimidine-Pyrimidine-CG-3', and 5'-Purine-Purine-CG-Pyrimidine-Pyrimidine-CG-3'; and
   b) detecting a biological activity of DNA-PK protein in the test sample, as compared to a control sample lacking the agent, wherein an increase or a decrease in the biological activity of DNA-PK indicates that the agent modulates a biological activity of DNA-PK, wherein the biological activity of DNA-PK is selected from activation of DNA-PKcs kinase activity and binding to Ku antigen.

* * * * *